US010737065B2

(12) United States Patent
Kanemasa et al.

(10) Patent No.: US 10,737,065 B2
(45) Date of Patent: Aug. 11, 2020

(54) MEDICAL DEVICE

(71) Applicant: SUMITOMO BAKELITE CO., LTD., Shinagawa-ku (JP)

(72) Inventors: Kenichi Kanemasa, Akita (JP); Shinetsu Harata, Akita (JP)

(73) Assignee: SUMITOMO BAKELITE CO., LTD., Shinagawa-ku (JP)

( * ) Notice: Subject to any disclaimer, the term of this patent is extended or adjusted under 35 U.S.C. 154(b) by 636 days.

(21) Appl. No.: 15/114,701

(22) PCT Filed: Jan. 28, 2015

(86) PCT No.: PCT/JP2015/052412
§ 371 (c)(1),
(2) Date: Jul. 27, 2016

(87) PCT Pub. No.: WO2015/115504
PCT Pub. Date: Aug. 6, 2015

(65) Prior Publication Data
US 2016/0339208 A1 Nov. 24, 2016

(30) Foreign Application Priority Data

Jan. 29, 2014 (JP) .................. 2014-014012
Jan. 7, 2015 (JP) .................. 2015-001800

(51) Int. Cl.
A61M 25/01 (2006.01)
(52) U.S. Cl.
CPC .... A61M 25/0147 (2013.01); A61M 25/0133 (2013.01); A61M 25/0136 (2013.01);
(Continued)

(58) Field of Classification Search
CPC ............. A61B 34/71; A61B 2034/301; A61B 2034/715; A61B 2017/2905;
(Continued)

(56) References Cited

U.S. PATENT DOCUMENTS 3,892,228 A 7/1975 Mitsui
5,462,527 A 10/1995 Stevens-Wright et al.
(Continued)

FOREIGN PATENT DOCUMENTS

JP 49-73286 6/1974
JP 56-158204 11/1981
(Continued)

OTHER PUBLICATIONS

International Search Report dated Apr. 21, 2015 in PCT/JP2015/052412, filed Jan. 28, 2015.

Primary Examiner — Bhisma Mehta
Assistant Examiner — William R Frehe
(74) Attorney, Agent, or Firm — Oblon, McClelland, Maier & Neustadt, L.L.P.

(57) ABSTRACT

A medical device is provided, including: a sheath portion (10); a pair of operation wires (30); and a turning operation portion (60) in which the sheath portion (10) is bent in a direction corresponding to the pulled one operation wire (30) through a turning operation. The turning operation portion (60) includes a wire fixation panel (64) around which the operation wires (30) are wound on a side peripheral surface; and a penetration portion (63c) and a closing portion (63d) which are provided further radially outwards than the side peripheral surface of the wire fixation panel (64) and at a position facing the side peripheral surface, so as to be integrated with the wire fixation panel (64).

19 Claims, 16 Drawing Sheets

(52) U.S. Cl.
CPC ... *A61M 25/0108* (2013.01); *A61M 2025/015* (2013.01); *A61M 2206/20* (2013.01)

(58) Field of Classification Search
CPC .. A61B 2017/2927; A61B 2017/00323; A61B 2017/00327; A61B 2017/2901–2905; A61B 2017/2912–2924; A61M 25/0136; A61M 2025/015; A61M 25/0108; A61M 25/0105; A61M 25/0133–0147
See application file for complete search history.

(56) References Cited

U.S. PATENT DOCUMENTS

| | | | | |
|---|---|---|---|---|
| 6,206,903 | B1* | 3/2001 | Ramans | A61B 17/29 606/205 |
| 2004/0199147 | A1* | 10/2004 | Nishizawa | A61B 17/062 606/1 |
| 2008/0312506 | A1* | 12/2008 | Spivey | A61B 1/00133 600/149 |
| 2009/0248053 | A1* | 10/2009 | Bacher | A61B 17/2909 606/170 |
| 2010/0001036 | A1* | 1/2010 | Marczyk | A61B 17/07207 227/175.1 |
| 2010/0286480 | A1* | 11/2010 | Peine | A61B 17/062 600/131 |
| 2011/0004157 | A1* | 1/2011 | Dewaele | A61B 1/00071 604/95.01 |
| 2011/0060349 | A1* | 3/2011 | Cheng | A61B 17/0469 606/139 |
| 2012/0172703 | A1* | 7/2012 | Esguerra | A61B 5/062 600/409 |
| 2013/0245676 | A1* | 9/2013 | Cappola | A61B 17/07207 606/213 |
| 2013/0324921 | A1* | 12/2013 | Reed | A61M 25/0136 604/95.04 |
| 2014/0200560 | A1* | 7/2014 | Lavender | A61B 17/00234 606/1 |
| 2015/0032151 | A1* | 1/2015 | Ishida | A61B 17/2909 606/205 |
| 2015/0127045 | A1* | 5/2015 | Prestel | A61B 17/29 606/208 |
| 2015/0231366 | A1* | 8/2015 | Davies | A61M 25/0147 604/95.04 |
| 2015/0265340 | A1* | 9/2015 | Munnig | A61B 18/1492 606/52 |
| 2017/0007344 | A1* | 1/2017 | Seow | A61B 34/71 |
| 2017/0245933 | A1* | 8/2017 | Graham | A61B 17/29 |
| 2017/0291008 | A1* | 10/2017 | Hillukka | A61M 25/00 |
| 2019/0076093 | A1* | 3/2019 | Saroha | A61M 25/0113 |

FOREIGN PATENT DOCUMENTS

| | | |
|---|---|---|
| JP | 2-53705 U | 4/1990 |
| JP | 5-507212 A | 10/1993 |
| JP | 8-38613 A | 2/1996 |
| JP | 2002-272676 A | 9/2002 |
| JP | 2005-230471 A | 9/2005 |
| JP | 2011-234900 A | 11/2011 |
| JP | 2013-153776 A | 8/2013 |
| JP | 2013-169226 A | 9/2013 |
| WO | 91/11213 A1 | 8/1991 |
| WO | WO 2013/140889 A1 | 9/2013 |

* cited by examiner

MEDICAL DEVICE

TECHNICAL FIELD

The present invention relates to a medical device.

Priority is claimed on Japanese Patent Application No. 2014-014012, filed Jan. 29, 2014 and Japanese Patent Application No. 2015-001800, filed Jan. 7, 2015, the content of which is incorporated herein by reference.

BACKGROUND ART

A catheter which can perform a bending operation on a distal portion by pulling an operation wire has been proposed. In a case of inserting this kind of catheter into a lumen in a living body such as a blood vessel, it is possible to select the insertion direction by bending the distal portion at a branch point of the lumen in a living body. In a case of a catheter with a comparatively large diameter, it is possible to bend the distal portion of the catheter in one direction by pushing a wire which has a large width and is used as an operation wire. In contrast, it is possible to bend the distal portion thereof in the other direction by drawing this wire.

In contrast, in a case of a catheter with a comparatively small diameter, in particular, a micro-catheter which has a small diameter and can be inserted into a peripheral blood vessel, an operation wire is extremely thin. Therefore, it is impossible to bend a distal portion even if the operation wire is pushed. This is because, even if the extremely thin operation wire is pushed, the extremely thin operation wire bends easily, and as a result, buckles, and therefore, it is impossible to transmit a sufficient pushing force to bend the distal portion of the catheter. Accordingly, in the case of a catheter such as a micro-catheter which has a small diameter, a distal portion of the catheter is bent by, in general, providing a plurality of operation wires arranged to face each other, and by selecting and pulling an operation wire positioned in a direction toward which bending is required, and loosening another operation wire so as to bend the pulled operation wire to the inside.

For this reason, in a catheter provided with a plurality of operation wires, in general, a turning operation is performed using an operation panel called a reel, a wheel, or the like so as to pull one operation wire, and at the same time, to loosen another operation wire.

As this kind of catheter, the following Patent document 1 is exemplified.

In Patent document 1, a catheter which has an adjustment function of adjusting the drawable amount of an operation wire in an initial state is disclosed in addition to the operation panel which pulls the operation wire as described above.

DOCUMENT LIST

Patent Document

Patent document 1: Japanese Unexamined Patent Application, First Publication No. 2013-153776

SUMMARY OF INVENTION

Technical Problem

In the catheter having a configuration of pulling one operation wire, and at the same time, loosening another operation wire as described above, if the pulling amount of one operation wire becomes large, the loosening amount of another operation wire also necessarily becomes large. Accordingly, in a case where the loosening amount exceeds a tolerance, there is a concern that the operation wire may deviate from the operation panel on which the operation wire is wound.

The present invention has been made in consideration of the above-described circumstances, and provides a medical device which prevents the operation wire which has been loosened through a turning operation from deviating.

Solution to Problem

A first aspect of the present invention is to provide the following medical device.

(1) A medical device including:

a sheath portion which is elongated and has flexibility;

a pair of operation wires which extend in the sheath portion and in which a distal end thereof is fixed to a distal portion of the sheath portion; and a turning operation portion which is provided on a proximal end side of the sheath portion, pulls one of the operation wires through a turning operation, and sends out the other operation wire through the turning operation to bend the sheath portion in a direction corresponding to the pulled one operation wire, in which the turning operation portion has a winding portion around which the operation wires are wound on a side peripheral surface, and a guard portion which is provided further radially outwards than the side peripheral surface and at a position facing the side peripheral surface, so as to be integrated with the winding portion.

It is preferable that the medical device (1) of a first aspect of the present invention further have the following characteristics. Specifically, it is preferable that the medical device have any of the following (2) to (20) or characteristics in which these are arbitrarily combined.

(2)

The turning operation portion has a fitting portion which is fitted to the winding portion in a turning shaft direction of the winding portion, the guard portion is included in the fitting portion, and the guard portion is disposed at a position facing the operation wires which have been wound around the side peripheral surface through fitting of the fitting portion to the winding portion, and is turnable integrally with the winding portion.

(3)

The winding portion includes a pair of flange portions formed on the side peripheral surface, and the guard portion is provided inside an inclusion circle which includes the flange portion and comes into contact with the outer peripheral surface of the flange portion around a rotation shaft of the winding portion.

(4)

Using a separation point at which the operation wires are separated from the side peripheral surface as a reference in an initial state, the guard portion extends by being biased to a side opposite to the direction in which the operation wires are drawn from the separation point to the sheath portion.

(5)

The operation wires, which are constituted of the same operation wires, are wound around the side peripheral surface over a winding angle which exceeds 360 degrees but does not reach 720 degrees in the initial state, and the guard portion extends by being biased to a side on which the winding using the operation wires is overlapping.

(6)

The winding portion includes a pair of fixation portions to which proximal sides of the pair of respective operation wires are individually fixed, and the guard portion rotates from one of the fixation portions to the other fixation portion.

(7)

The distance from the inner peripheral surface of the guard portion to the side peripheral surface is made shorter than that to other portions in the vicinity of the fixation portion.

(8)

The winding portion has a pair of flange portions which are formed so as to pinch the side peripheral surface, and a notch which is formed inward from the outer peripheral side in one of the flange portions, in which the fixation portion is formed on one surface of the one of the flange portions on a side opposite to the surface facing the other flange portion, the operation wires wound around the side peripheral surface are bound to the fixation portion by being drawn from the notch, and the guard portion faces the operation wire wound around the side peripheral surface and also faces the operation wire bound to the fixation portion.

(9)

The fixation portion is bent to the radial outside of the flange portion, the guard portion abuts or approaches the distal portion of the fixation portion and the outer peripheral surface of the flange portion, and the proximal side of the operation wire is inserted into a region surrounded by the fixation portion, the flange portion, and the guard portion, and is bound to the fixation portion.

(10)

The winding portion includes a pair of flange portions formed on the side peripheral surface, and the gap between the inner peripheral surface of the guard portion and the outer peripheral surface of the flange portion is smaller than the diameter dimension of the operation wire.

(11)

The winding portion includes the side peripheral surface, the pair of flange portions formed on the side peripheral surface, and an opening portion provided in at least one of the flange portions, and the guard portion is a projection portion which penetrates the opening portion.

(12)

In the winding portion, the pair of flange portions are formed so as to pinch the side peripheral surface, and the opening portions are provided so as to face both of the pair of flange portions, and the guard portion includes a penetration portion which is provided from the one opening portion to the other opening portion in a turning shaft direction of the side peripheral surface.

(13)

When the turning operation reaches a predetermined angle, the penetration portion abuts on the other operation wire which has been sent out through the turning operation, and the other operation wire is pulled in the rotation direction of the turning operation through the turning operation further exceeding the predetermined angle.

(14)

The medical device further includes: a pulling amount-limiting portion which operates according to a reaction force received from the operation wire through the turning operation and limits the pulling of the operation wire to be less than or equal to a predetermined amount, in which a reaction force which the turning operation portion receives from the one operation wire due to the turning operation and a reaction force which the turning operation portion receives from the other operation wire which has entered a tensed state by being pulled in the rotation direction due to the turning operation are imparted in the same direction.

(15)

A notch is formed in the winding portion as an opening portion inward from the outer peripheral side of the flange portion, and an end portion of the operation wire drawn from the notch is fixed to the winding portion, and the guard portion includes a closing portion which closes an outer peripheral side than the side peripheral surface in the notch.

(16)

The penetration portion is provided from the notch over the other opening portion, the closing portion closes an outer peripheral side than the position of the penetration portion in the notch, and the gap between the notch and the closing portion is smaller than the diameter dimension of the operation wire.

(17)

A plurality of notches are formed in the flange portion, the pair of operation wires are fixed to the winding portion by being respectively drawn from different notches, and the guard portion is formed with respect to each of the plurality of the notches from which the operation wires are drawn.

(18)

A notch is formed in the winding portion as the opening portion inward from the outer peripheral side of the flange portion, and end portions of the operation wires which are drawn from the notch are fixed to the winding portion, and, using a separation point at which the operation wires are separated from the side peripheral surface as a reference in an initial state, opening portions which are different from the notch are formed in the flange portion on a side opposite to a direction in which the operation wires are drawn from the separation point to the sheath portion, and the penetration portion penetrates the opening portions.

(19)

The guard portion includes a closing portion which closes the notch, and the gap between the notch and the closing portion is smaller than the diameter dimension of the operation wire.

(20)

The medical device further includes: angle-restricting mechanisms which are engaged with each other due to a turning operation reaching a predetermined rotation angle and restrict the turning operation.

Advantageous Effects of Invention

According to the present invention, it is possible to provide a medical device which prevents operation wires which have been loosened through a turning operation from deviating.

DESCRIPTION OF EMBODIMENTS

Figure 1A:
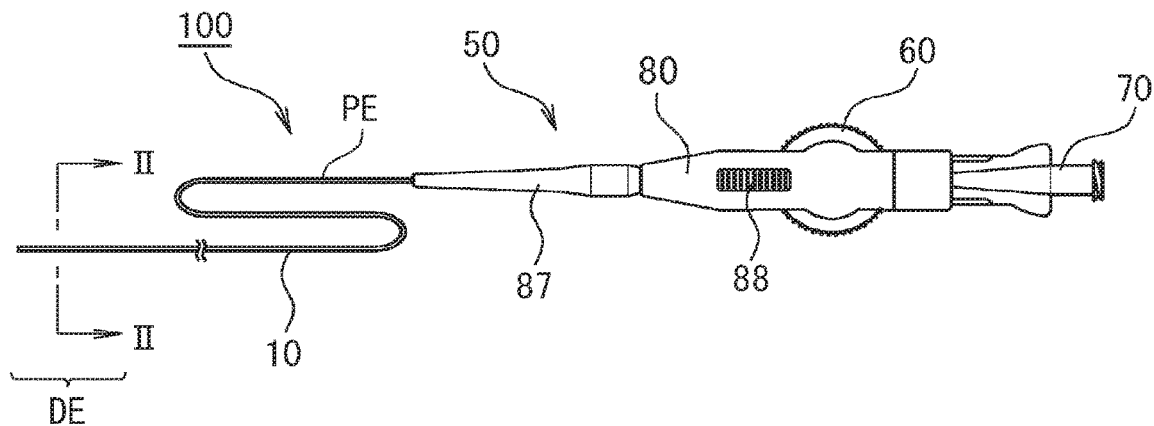
FIG. 1A is a schematic plan view of a catheter showing an example of a first embodiment of the present invention.

Hereinafter, examples of preferred embodiments of the present invention will be described using drawings. In all of the drawings, the same reference numerals are given to the same components and the description thereof will not be repeated. In addition, in the following description, with respect to the terms "top" and "bottom", the side shown in FIG. 1 is referred to as the top (or the upper part) of a catheter 100 and the opposite side thereof is referred to as the bottom (lower part) of the catheter 100 unless otherwise specified.

The present invention is not limited to the following examples. For example, these examples or preferred components of embodiments may be appropriately combined, or the present invention may be combined with other components as long as there are no problems. It is also possible to change and/or add to or omit with respect to the numbers, the positions, the sizes, materials, or the like as necessary within the scope of the present invention. In addition, in some cases, the proportion or the size of members in the drawings is changed in order to facilitate checking.

First Embodiment

First, an outline of the catheter 100 of a first embodiment of the present invention will be described.

The catheter 100 of the first embodiment will be described using FIGS. 1A to 1C and FIGS. 4 to 9B.

Figure 1B:
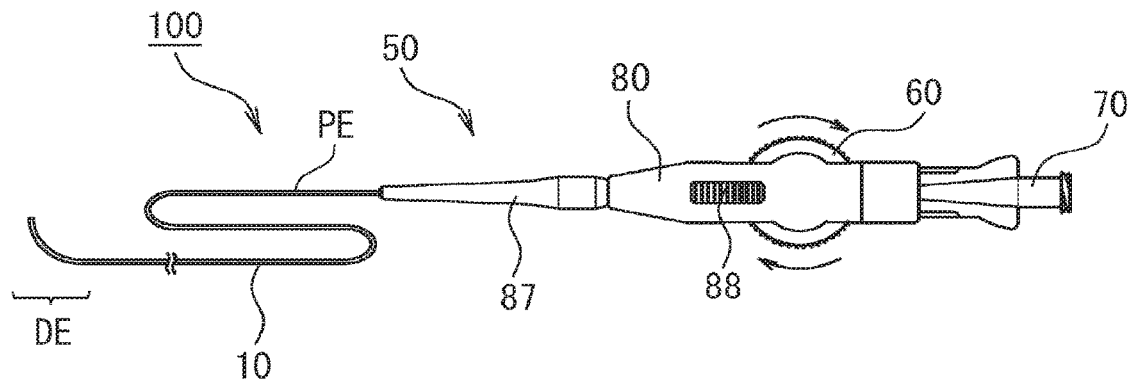
FIG. 1B is a schematic plan view of the catheter showing a state in which the catheter shown in FIG. 1A operates in one direction through a turning operation.
Figure 1C:
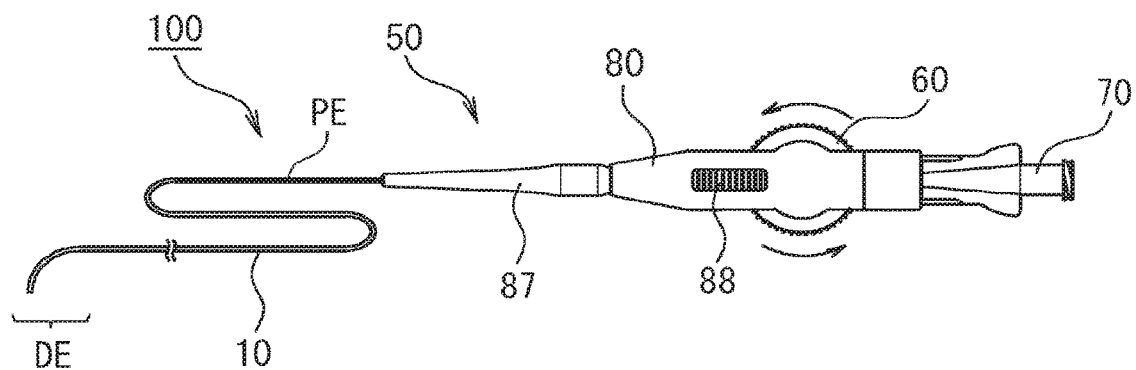
FIG. 1C is a schematic plan view of the catheter showing a state in which the catheter shown in FIG. 1A operates in the other direction through a turning operation.

FIG. 1A is a plan view showing the catheter 100 according to the present embodiment of the present invention. FIG. 1B is a plan view showing a state in which a sheath portion of the catheter 100 operates in one direction through a turning operation. FIG. 1C is a plan view showing a state in which the sheath portion of the catheter 100 operates in the other direction through a turning operation.

Figure 4:
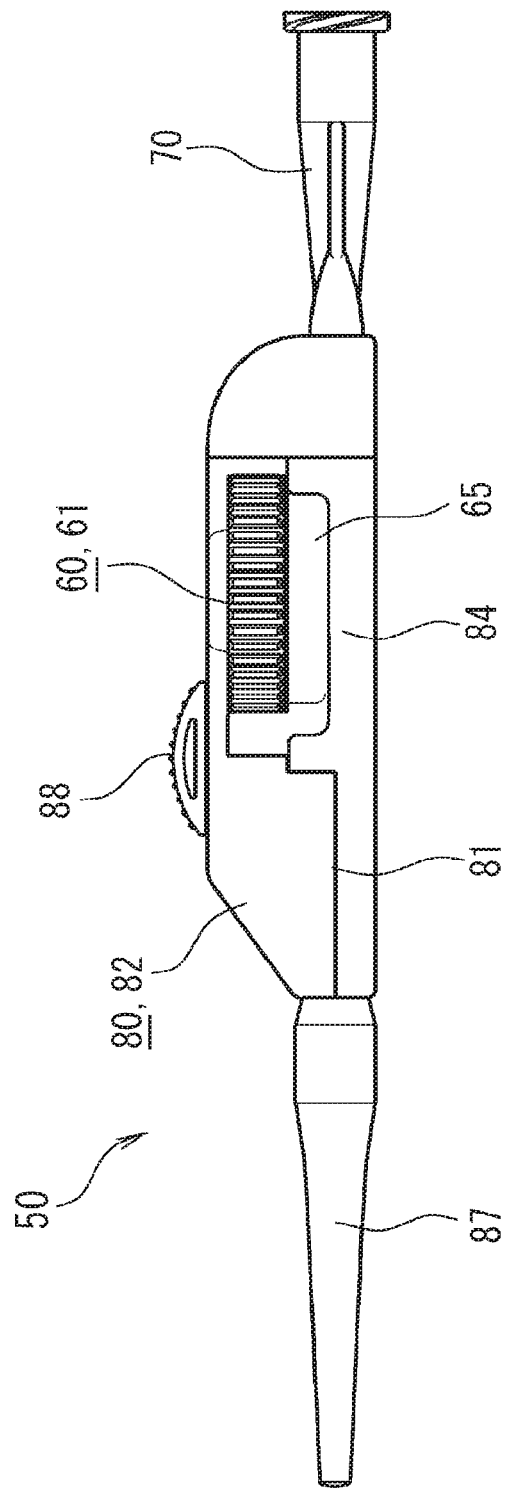
FIG. 4 is a schematic side view of an operation portion of the catheter shown in FIG. 1A.

FIG. 4 is a schematic side view of an operation portion 50 of the catheter 100.

Figure 5:
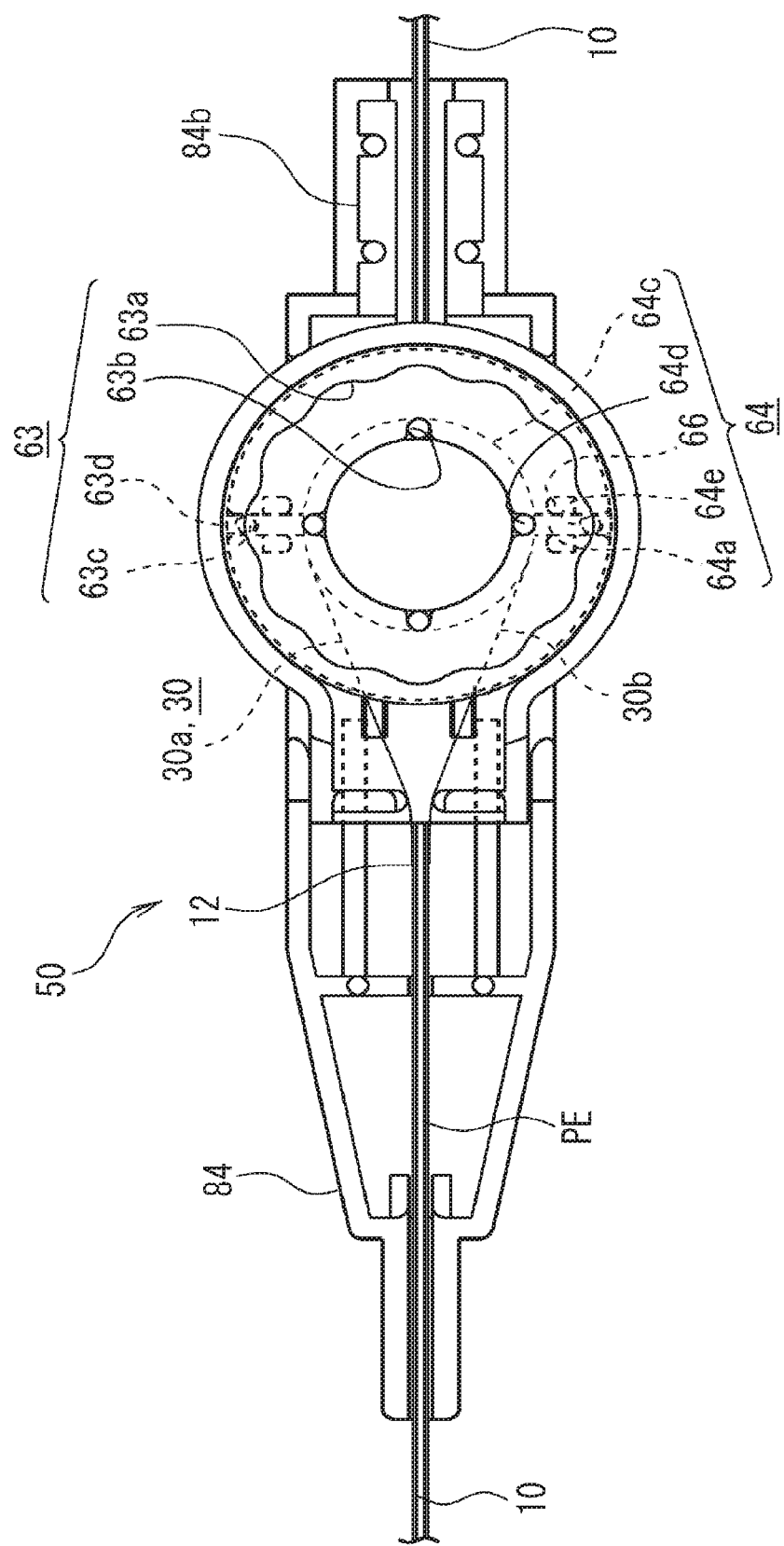
FIG. 5 is a schematic plan view of the catheter shown in FIG. 1A which illustrates an inner structure of the operation portion and from which several upper parts are excluded.

FIG. 5 is a schematic plan view illustrating an inner structure of the operation portion 50.

Figure 6:
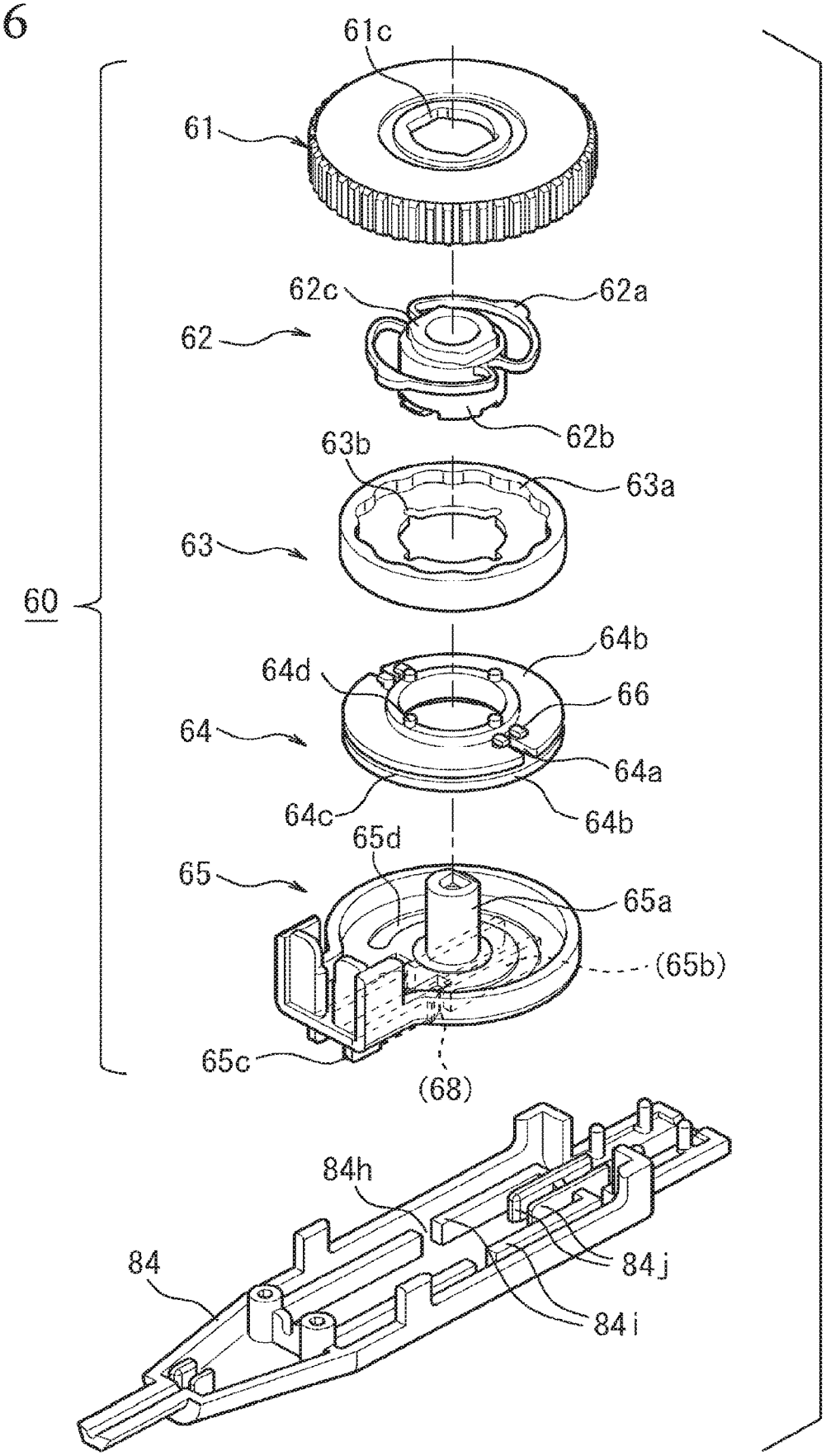
FIG. 6 is an exploded schematic perspective view from which several upper parts are excluded and in which a lower main body of the catheter in FIG. 1A and an exploded turning operation portion are viewed from above.

FIG. 6 is an exploded schematic perspective view in which a lower main body 84 and a turning operation portion 60 in the first embodiment is viewed from above.

Figure 7:
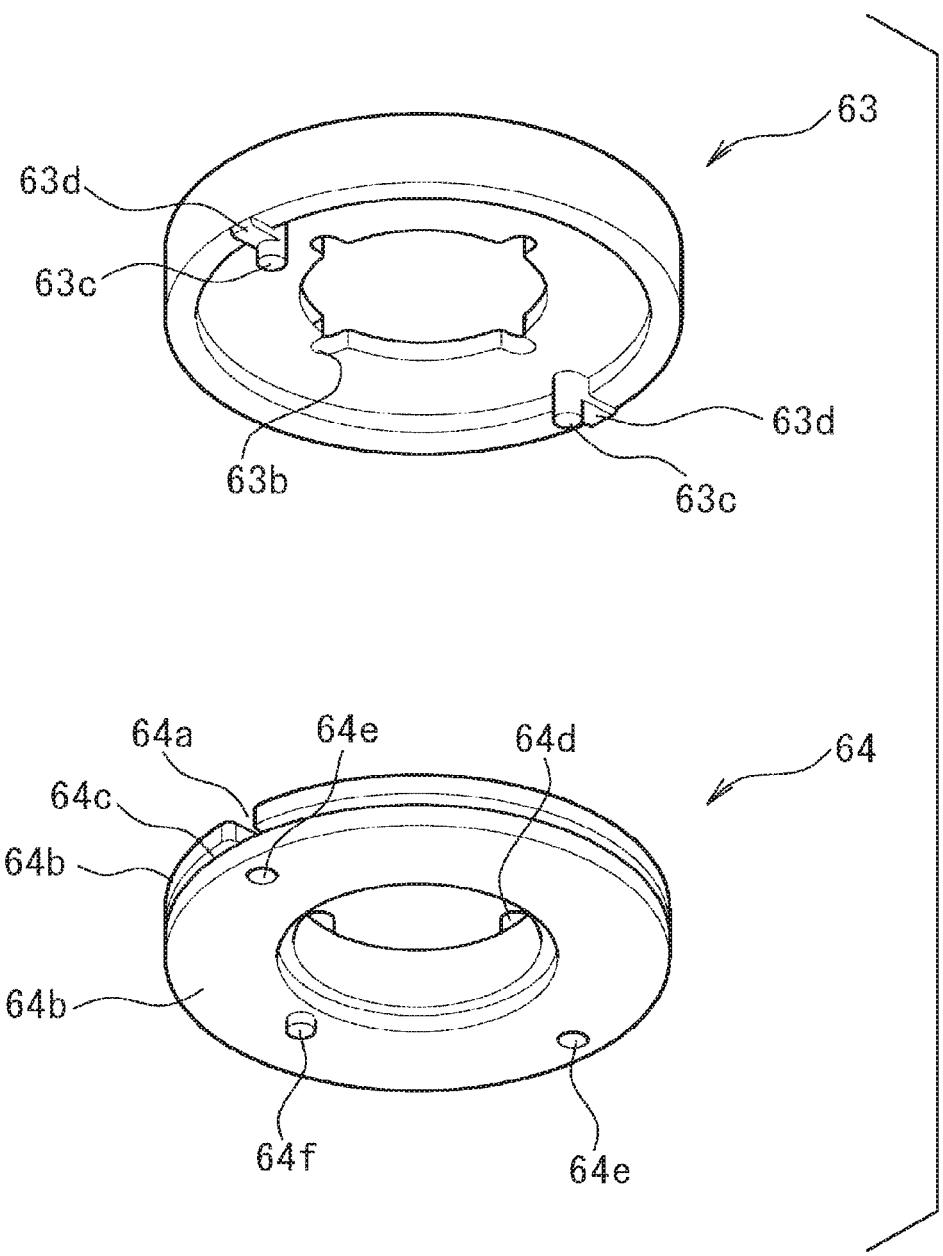
FIG. 7 is a schematic perspective view of the catheter shown in FIG. 1A in which an engagement member and a wire fixation panel are viewed from below.

FIG. 7 is a schematic perspective view in which an engagement member 63 and a wire fixation panel 64 in the first embodiment are viewed from below.

Figure 8A:
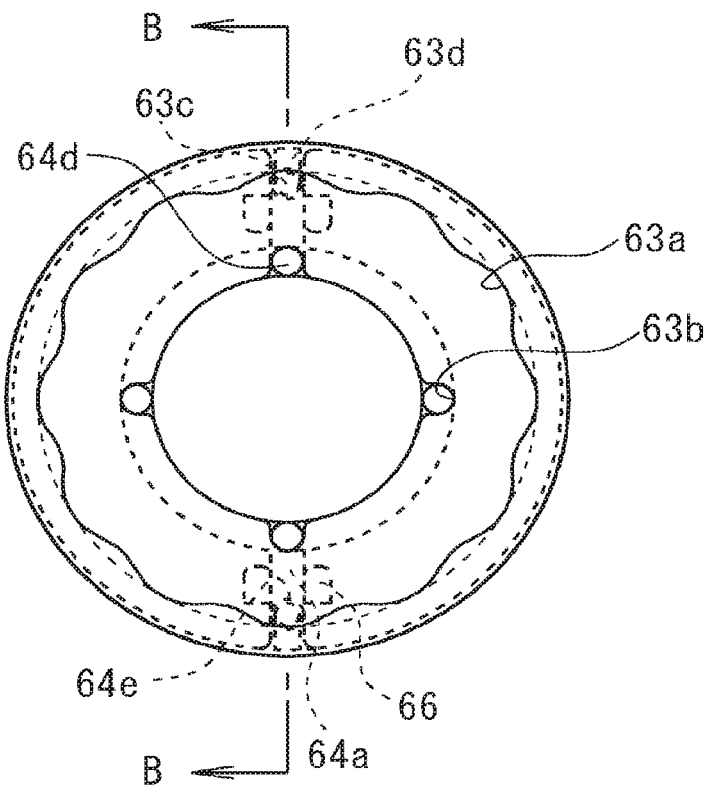
FIG. 8A is a schematic plan view of the catheter shown in FIG. 1A in which a state in which the engagement member and the wire fixation panel are combined is viewed from above.
Figure 8B:
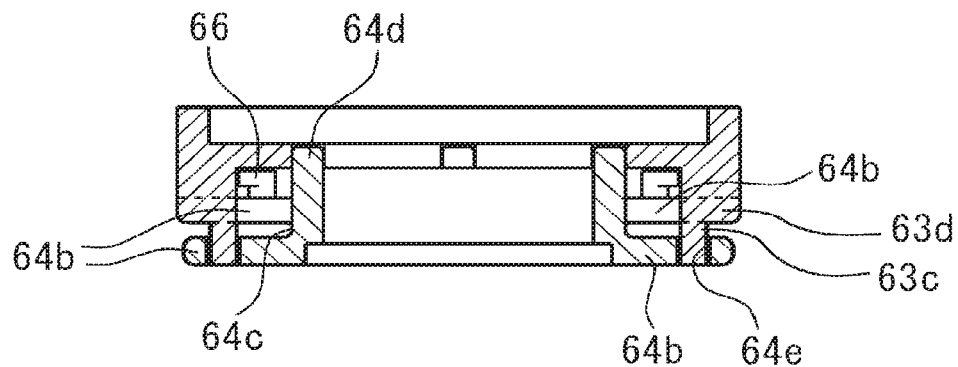
FIG. 8B is a cross-sectional view of line B-B of the combination of the engagement member and the wire fixation panel shown in FIG. 8A.

FIGS. 8A to 8C are a schematic plan view and a cross-sectional view showing a state in which the engagement member and the wire fixation panel of the catheter shown in FIG. 1A are combined.

Figure 9A:
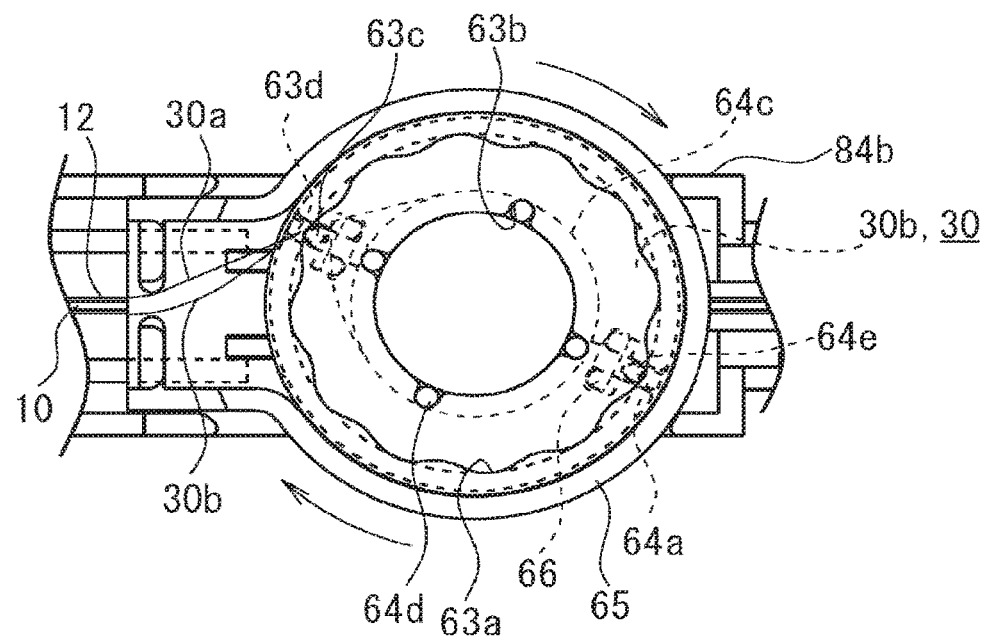
FIG. 9A is a view showing a state in which an operation wire is loosened in the wire fixation panel when a turning operation of the catheter shown in FIG. 1A is performed clockwise.
Figure 9B:
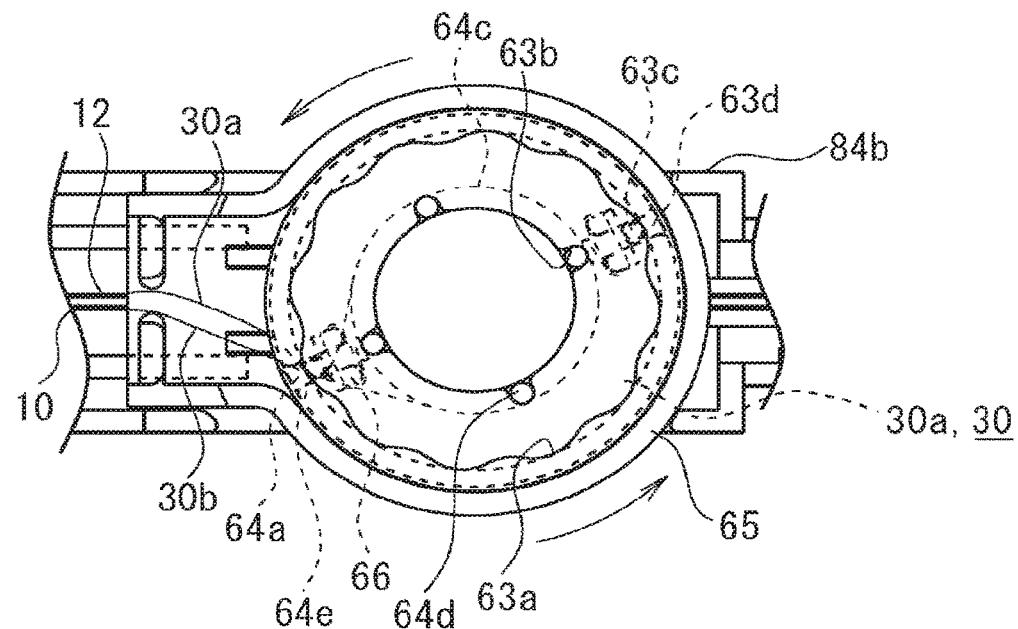
FIG. 9B is a view showing a state in which an operation wire is loosened in the wire fixation panel when a turning operation of the catheter shown in FIG. 1A is performed counterclockwise.

FIGS. 9A and 9B are views showing a state in which a turning operation of the catheter shown in FIG. 1A is performed.

As shown in FIG. 1A and FIG. 5, a medical device (for example, the catheter 100) according to the present embodiment includes a sheath portion 10, a pair of operation wires 30 (30a and 30b), and a turning operation portion 60.

The turning operation portion 60 has the engagement member 63, the wire fixation panel 64, and a shaft member 65 as shown in FIG. 5 or 6. The turning operation portion 60 has a wrapping portion 64c as a winding portion, and a penetration portion 63c and a closing portion 63d as a guard portion.

The sheath portion 10 is elongated and has flexibility.

A pair of operation wires 30 extend in the sheath portion 10 and distal ends of the operation wires are disposed at a distal portion DE of the sheath portion 10.

The turning operation portion 60 is provided on a proximal end side of the sheath portion 10, pulls one of the operation wires 30 through a turning operation, and sends out the other operation wire 30 through the turning operation to bend the sheath portion 10 in a direction corresponding to the pulled one operation wire 30. The proximal end side of the sheath portion 10 means a side close to the operation portion 50.

The wire fixation panel 64 (winding portion) has the wrapping portion 64c (side peripheral surface) as shown in FIG. 6 or 7 around which the operation wire 30 is wound.

The engagement member 63 has the penetration portion 63c and the closing portion 63d (guard portion) which are provided further radially outwards than the wrapping portion 64c and at a position facing the wrapping portion 64c, so as to be integrated with the wire fixation panel 64. In FIG. 7, the guard portion is disposed on a straight line passing through the center of the circular engagement member and at two positions separated from each other.

Even if the turning operation is performed using the above-described structure, the relative position between the winding portion (wire fixation panel 64) and the guard portion (the penetration portion 63c and the closing portion 63d) does not change. The guard portion exists outside a region (wrapping portion 64c) around which the operation wire 30 is wound and at a position facing the region regardless of the turning operation. For this reason, the guard portion can catch or press the operation wire 30 wound around the region. Accordingly, the operation wire 30 loosened from the winding portion through the turning operation can be prevented from deviating from the winding portion.

The "winding portion" refers to a member around which the operation wire 30 is wound on the side peripheral surface thereof and which is rotated through a turning operation performed for bending the sheath portion 10. In the present embodiment, the wire fixation panel 64 is the winding portion and the wrapping portion 64c is the side peripheral surface thereof.

In addition, the "guard portion" refers to a member which is provided so as to be integrated with the winding portion in order to prevent deviation of the operation wire 30. As an example of an aspect in which the winding portion and the guard portion are integrally provided, the winding portion and the guard portion may be an originally integrated member or may be individual members before being assembled. In addition, in the aspect, the winding portion and the guard portion may be directly bonded to each other or may be connected to each other through another member, after being assembled (finished product).

The "position facing the side peripheral surface" refers to a position viewed from the side peripheral surface (wrapping portion 64c) and is not necessarily limited to the position straightly facing the side peripheral surface. Accordingly, the position at which the guard portion (the penetration portion 63c and the closing portion 63d) is provided is not limited to the position included in the wire fixation panel 64 as in this embodiment and may be on the outside of the wire fixation panel 64 as long as it is possible to achieve the purpose.

As shown in FIGS. 1A, 4, and 5, the operation portion 50 includes an operation portion main body 80 which is mounted at a proximal portion PE of the sheath portion 10; and the turning operation portion 60 which individually imparts a pulling force to a plurality of operation wires 30a and 30b through a turning operation.

The operation portion main body 80 is a housing which is gripped by the hands of a user. In FIG. 1A, the proximal portion PE of the sheath portion 10 is protected by a tubular protector 87 and is introduced inside the operation portion main body 80.

In the operation portion main body 80, the turning operation portion 60 (a dial operation portion 61, the shaft member 65, or the like) is pinched by an upper main body 82 and the lower main body 84 in a vertical direction as shown in FIG. 4. A separation surface 81 corresponds to a junction surface between the upper main body 82 and the lower main body 84.

As shown in FIG. 1A, the operation portion 50 further includes a hub connector 70 in addition to the operation portion main body 80 and the turning operation portion 60. The hub connector 70 is mounted at a rear end portion of the operation portion main body 80. The most proximal end (proximal end) of sheath portion 10 is connected to the hub connector 70 such that these communicate with each other. A syringe (not shown in the drawing) is mounted from the rear side (right side in FIG. 1A) of the hub connector 70. By injecting a drug solution or the like into the hub connector 70 using the syringe, it is possible to supply the drug solution or the like to the inside of a lumen in a living body of a subject through a main lumen 20 (refer to FIGS. 2 and 3) of the sheath portion.

The dimension of the operation portion 50, that is, the dimension from the distal end of the protector 87 to the rear end of the hub connector 70 can be arbitrarily selected, but is preferably about 5 cm to 15 cm.

Next, an outline of an operation of the catheter 100 will be described.

Figure 2:
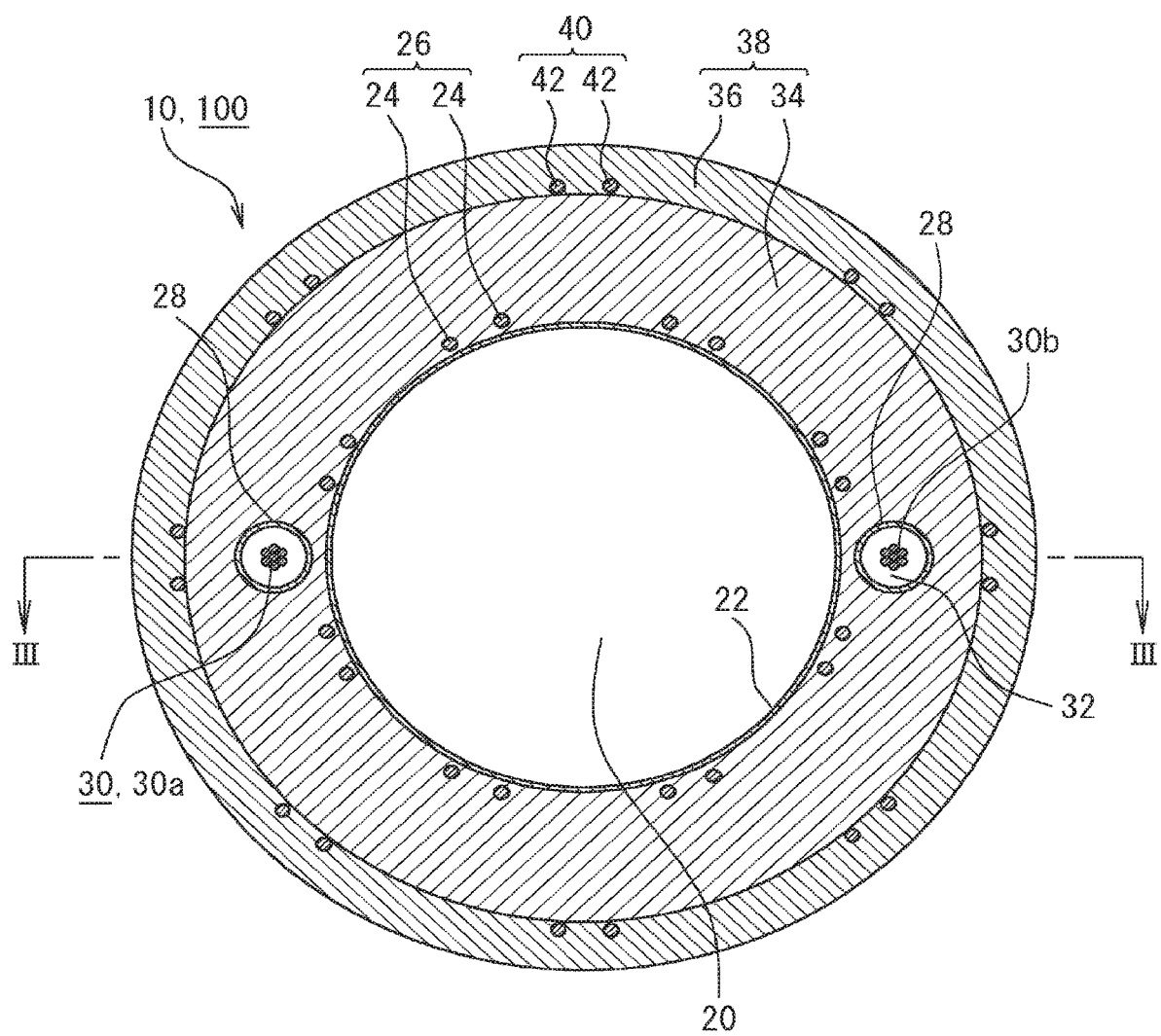
FIG. 2 is a schematic cross-sectional view of line II-II of the catheter shown in FIG. 1A.
Figure 3:
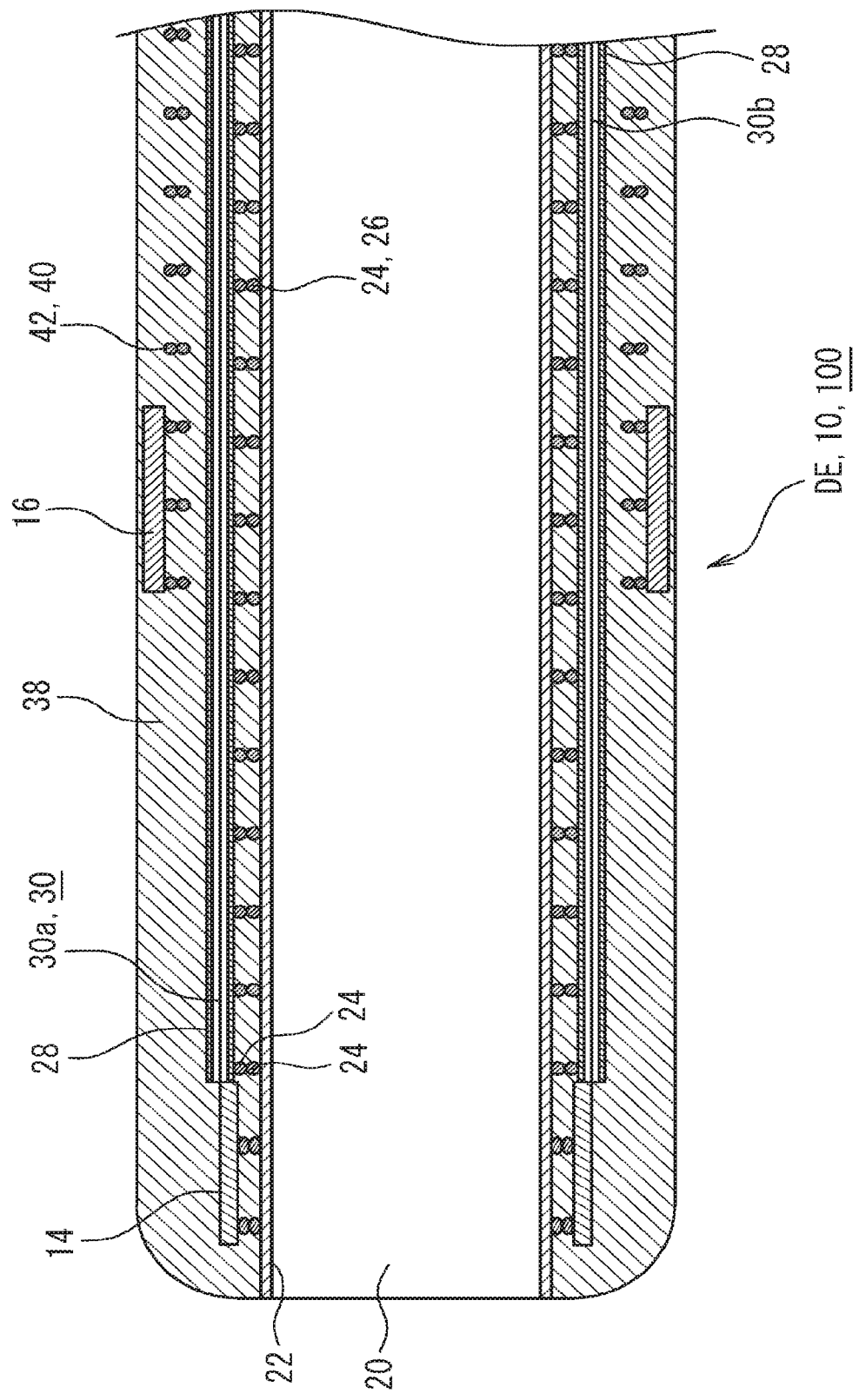
FIG. 3 is a schematic longitudinal cross-sectional view of a distal portion DE of the catheter shown in FIG. 1A and is a schematic cross-sectional view of line of the catheter shown in FIG. 2.

As shown in FIGS. 2 and 3, the operation wires 30a and 30b are inserted into the sheath portion 10. The operation wires 30a and 30b are drawn from the sheath portion 10 to the side within the operation portion main body 80 and are directly or indirectly connected to the turning operation portion 60. The sheath portion 10 from which the operation wires 30a and 30b are drawn can be connected to the hub connector 70 as described above.

The turning operation portion 60 of the present embodiment is rotatable with respect to the operation portion main body 80. The rotation amount or the rotation angle of the turning operation portion 60 is arbitrarily selected. In the present embodiment, the rotation and the turn are not distinguished from each other. When the turning operation portion 60 is rotated in one direction, a first operation wire 30a is tensed and a second operation wire 30b is relaxed. When the turning operation portion 60 is rotated in the other direction, the second operation wire 30b is tensed and the first operation wire 30a is relaxed. The operation wires 30a and 30b are independently fixed to the distal portion DE. For this reason, the pulled operation wires 30a and 30b bend the distal portion DE of the catheter 100.

Specifically, when the turning operation portion 60 is rotated in one direction (clockwise) as shown in FIG. 1B, the first operation wire 30a (refer to FIG. 3) is pulled to the proximal side and the distal portion DE of the sheath portion 10 is bent. When the turning operation portion 60 is rotated in the other direction (counterclockwise) around a rotation shaft as shown in FIG. 1C, the second operation wire 30b is pulled to the proximal side and the distal portion DE is reversely bent. In this manner, by selectively pulling the two operation wires 30a and 30b, it is possible to selectively bend the distal portion DE of the catheter 100 in a first or second direction which are mutually included in an identical plane.

The bending of the sheath portion 10 includes an aspect in which the sheath portion 10 is folded and an aspect in which the sheath portion is curved in a bow-like manner.

In the case of the operation portion 50 in which when one of a pair of operation wires 30a and 30b is loosened as in the present embodiment, the other is pulled, a mechanism for loosening the operation wires 30a and 30b, which are formed of a plurality of wires, together is required. The present embodiment realizes this through transition of the turning operation portion 60.

A recess-projection engagement portion (a structure having a peak portion and a valley portion) is formed on the peripheral surface of the turning operation portion 60 (dial operation portion 61: refer to FIG. 6). A lock slider 88 which can come into contact with and be separated from the turning operation portion 60 is provided in the operation portion main body 80. When the lock slider 88 is slid toward the turning operation portion 60, the lock slider and the turning operation portion are engaged with each other to restrict the rotation of the turning operation portion 60. Accordingly, it is possible to maintain a bent state of the catheter 100 by restricting the rotation of the turning operation portion 60 through an operation of the lock slider 88 in a state of FIG. 1B or 1C in which the distal portion DE of the catheter 100 is bent.

Structure of Sheath Portion 10

Next, the structure of the sheath portion 10 will be described.

FIG. 2 is a transverse cross-sectional view of the catheter 100 in FIG. 1A and is a cross-sectional view of line II-II.

FIG. 3 is a longitudinal cross-sectional view of the distal portion DE of the catheter 100 in FIG. 1A and is a cross-sectional view of line III-III in FIG. 2.

The catheter 100 of the present embodiment is an intravascular catheter which is used by inserting the sheath portion 10 into a blood vessel. The sheath portion 10 is a hollow tubular elongated member in which the main lumen 20 is formed as a through-hole. It is preferable that the sheath portion 10 be formed to have a sufficient outer diameter and a sufficient length to enter any of eight sub-segments of the liver. The outer diameter of the distal portion DE of the sheath portion 10 is preferably less than 1 mm. The catheter 100 of the present embodiment can be used as a micro-catheter which can be inserted into peripheral blood vessels.

The sheath portion 10 has the main lumen 20; and a plurality of sub-lumens 32 which have a smaller diameter than that of the main lumen 20 and into which a plurality of operation wires 30a and 30b are inserted. The number of operation wires 30a and 30b and the number of sub-lumens can be arbitrarily selected.

The sheath portion 10 includes a wire-reinforced layer 26 which is formed by winding a reinforcement wire 24 around the main lumen 20; a hollow tube 28 which is buried outside this wire-reinforced layer 26, defines a sub-lumen 32 having a smaller diameter than that of the main lumen 20, and is made of resin; and an outer layer 38 which includes the wire-reinforced layer 26 and the hollow tube 28 and is made of resin.

The sheath portion 10 has a stacked structure. The sheath portion 10 is constituted such that an inner layer 22, a first outer layer 34, and a second outer layer 36 are stacked around the main lumen 20 in order from the inner diameter side. It is preferable that a hydrophilic layer (not shown in the drawing) be formed on the outer surface of the second outer layer 36. The inner layer 22, the first outer layer 34, and the second outer layer 36 are formed of a flexible resin material, have an annular shape, and have a substantially even thickness. In some cases, the first outer layer 34 and the second outer layer 36 are collectively called the outer layer 38.

The inner layer 22 is an innermost layer of the sheath portion 10 and defines the main lumen 20 using the inner wall surface thereof. The transverse cross-sectional shape of the main lumen 20 is not particularly limited and can be arbitrarily selected, but is a circular shape in the present embodiment. In the case of the main lumen 20 with a transverse cross-sectional circular shape, the diameter thereof may be even over the longitudinal direction of the sheath portion 10, or may differ depending on the longitudinal direction. For example, the sheath portion 10 may have a tapered shape in which the diameter of the main lumen 20 is continuously enlarged from the distal end to the proximal end in a partial or whole length region thereof.

The material of the inner layer 22 can be arbitrarily selected, and examples thereof include a fluorine-based thermoplastic polymer material. Specific examples of the fluorine-based thermoplastic polymer material include polytetrafluoroethylene (PTFE), polyvinylidene fluoride (PVDF), and perfluoroalkoxy fluorine resin (PFA). Using the inner layer 22 formed of such a fluorine-based polymer material, the delivery properties when supplying a drug solution or the like through the main lumen 20 are improved. In addition, in a case where a guide wire is inserted into the main lumen 20, the sliding resistance of the guide wire is decreased.

The wire-reinforced layer 26 and the hollow tube 28 are buried inside the first outer layer 34 corresponding to the inner layer of the outer layer 38 in order from the inner side diameter side. A second reinforced layer 40 is provided inside the second outer layer 36 corresponding to the outer side layer of the outer layer 38. The second reinforced layer 40 comes into contact with the outer surface of the first outer layer 34. The wire-reinforced layer 26 and the second reinforced layer 40 are disposed coaxially with the sheath portion 10. The second reinforced layer 40 is disposed away from the wire-reinforced layer 26 and the hollow tube 28 so as to enclose the periphery of the wire-reinforced layer and the hollow tube.

The material of the outer layer 38 can be arbitrarily selected. However, it is possible to preferably use a thermoplastic polymer material. Examples of this thermoplastic polymer material include polyimide (PI), polyamideimide (PAI), a polyethylene terephthalate (PET), polyethylene (PE), polyamide (PA), polyamide elastomer (PAE), nylon elastomer such as polyether block amide (PEBA), polyurethane (PU), ethylene-vinyl acetate resin (EVA), polyvinyl chloride (PVC), or polypropylene (PP).

Inorganic filler may be mixed with the outer layer 38. Examples of the inorganic filler include a contrast agent such as barium sulfate or bismuth subcarbonate. By mixing the contrast agent with the outer layer 38, it is possible to improve X-ray contrast properties of the sheath portion 10 in a lumen in a living body.

The first outer layer 34 and the second outer layer 36 contain the same or different kinds of resin materials. In FIG. 2, a boundary surface between the first outer layer 34 and the second outer layer 36 is clearly expressed, but the present invention is not limited thereto. In a case where the first outer layer 34 and the second outer layer 36 are formed of the same kind of resin material, the boundary surface between both layers may be harmoniously integrated and fused. That is, the outer layer 38 of the present embodiment may be formed of multiple layers in which the first outer layer 34 and the second outer layer 36 are distinguishable from each other, or may be formed of a single layer in which the first outer layer 34 and the second outer layer 36 are integrated.

The hydrophilic layer formed on the outer surface of the second outer layer 36 constitutes the outermost layer of the catheter 100. Although the hydrophilic layer is not shown in FIG. 2, the hydrophilic layer may be considered as the surface of the catheter 100 in FIG. 1A or the like. The hydrophilic layer may be formed in the whole length of the sheath portion 10, or in a partial length region on the distal side including the distal portion DE. The hydrophilic layer may be formed of an arbitrary material, and for example, comprise a hydrophilic resin material such as a maleic anhydride-based polymer such as polyvinyl alcohol (PVA) or a copolymer thereof, and polyvinylpyrrolidone.

The wire-reinforced layer 26 is a protection layer which protects the inner layer 22 by being provided further toward the inner diameter side than the operation wire 30 in the sheath portion 10. The wire-reinforced layer 26 existing further toward the inner diameter side than the operation wire 30 prevents breakage of the first outer layer 34 and the inner layer 22 due to the operation wire 30 and exposure of the operation wire to the main lumen 20.

The wire-reinforced layer 26 is formed by winding the reinforcement wire 24. As the material for the reinforcement wire 24, it is possible to use resin materials such as polyimide (PI), polyamideimide (PAI), or polyethylene terephthalate (PET) which has a higher shear strength than those of the inner layer 22 and the first outer layer 34, in addition to metal materials such as tungsten (W), stainless steel (SUS), nickel-titanium alloy, steel, titanium, copper, titanium alloy, or copper alloy. In the present embodiment, a thin stainless steel wire is exemplified as the reinforcement wire 24.

The wire-reinforced layer 26 is formed by braiding the reinforcement wire 24 in a coil-wound shape or a mesh shape. The number of reinforcement wires 24, the coil pitch, and the number of meshes can be arbitrarily selected, and are not particularly limited. The wire-reinforced layer 26 of the present embodiment is a braid layer in which multiple reinforcement wires 24 are braided in a mesh shape.

The hollow tube 28 is a hollow tubular member which defines the sub-lumen 32. The hollow tube 28 is buried inside the first outer layer 34. The hollow tube 28 can be formed of, for example, a thermoplastic polymer material. Examples of the thermoplastic polymer material include low-friction resin materials such as polytetrafluoroethylene (PTFE), polyetheretherketone (PEEK), or tetrafluoroethylene-hexafluoropropylene copolymer (FEP).

The hollow tube 28 is formed of a material which has higher bending rigidity and tensile elastic modulus than those of the outer layer 38.

As shown in FIG. 2, two hollow tubes 28 are disposed around the wire-reinforced layer 26 so as to face each other at 180°, and the operation wires 30 (30*a* and 30*b*) are respectively inserted into these two hollow tubes 28. The two hollow tubes 28 are parallel to the shaft center direction of the sheath portion 10.

As shown in FIG. 2, the two hollow tubes 28 are disposed on the same circumference so as to surround the main lumen 20. Instead of the present embodiment, three or four hollow tubes 28 may be disposed around the main lumen 20. In this case, the operation wires 30 may be disposed in all of the hollow tubes 28, or in some of the hollow tubes 28.

An operation wire 30 is loosely inserted into a hollow tube 28 so as to be slidable with respect to the hollow tube. The distal portion of an operation wire 30 is fixed to the distal portion DE of the sheath portion 10. By pulling the operation wire 30 to the proximal side, the sheath portion 10 is bent since a tensile force is imparted at a position eccentric from the shaft center of the sheath portion 10.

The operation wire 30 of the present embodiment is extremely thin and has high flexibility. Therefore, a pushing force is not substantially imparted to the distal portion DE of the sheath portion 10 even if the operation wire 30 is pushed to the distal end side. In addition, in the operation wire 30, loosening is easily caused by a turning operation.

The operation wire 30 may be constituted of a single wire material, or may be a stranded wire which is constituted such that a plurality of fine wires are mutually stranded. The number of fine wires constituting one stranded wire of the operation wire 30 is not particularly limited, but is preferably greater than or equal to three. A suitable example of the number of fine wires is seven or three.

Examples of the operation wire 30 include metal wires such as low carbon steel (piano wire), stainless steel (SUS), a steel wire which is subjected to corrosion-resistant coating, titanium or titanium alloy, or tungsten. In addition, as the operation wire 30, it is also possible to use polyvinylidene fluoride (PVDF), high-density polyethylene (HDPE), poly (para-phenylene benzobisoxazole) (PBO), poly etheretherketone (PEEK), polyphenylene sulfide (PPS), polybutylene terephthalate (PBT), polyimide (PI), polytetrafluoroethylene (PTFE), or polymer fibers such as boron fibers.

In the catheter 100 of the present embodiment, two operation wires 30 are respectively inserted into the hollow tubes 28 and are individually fixed to the distal portion DE of the sheath portion 10. Regarding the two operation wires 30, two wires may be individually formed, or one wire may be folded at the distal portion DE of the sheath portion 10 so as to be individually pulled in the turning operation portion 60 from the ends thereof. That is, the operation wires 30 being plural or two in the present embodiment means that there are a plurality of or two paths imparting a pulling force which bends the distal portion DE of the sheath portion 10.

In a case where two operation wires 30 are constituted by folding one wire at the distal portion DE of the sheath portion 10, the distal end of the operation wire 30 refers to a folded portion of the wire at the distal portion DE.

The second reinforced layer 40 is a protection layer which is provided further toward an outer peripheral side than the operation wire 30 in the sheath portion 10 and protects the second outer layer 36. The second reinforced layer 40 existing on the outer peripheral side of the operation wire 30 prevents breakage of the second outer layer 36 and the hydrophilic layer (not shown in the drawing) due to the operation wire 30 and exposure of the operation wire to the outside of the sheath portion 10.

The second reinforced layer 40 is formed by braiding a second reinforcement wire 42 in a coil-wound shape or a mesh shape. It is possible to use the above-described materials which have been exemplified as the reinforcement wire 24 of the wire-reinforced layer 26, as the second reinforcement wire 42. The second reinforcement wire 42 and the reinforcement wire 24 may be the same or different kinds of materials. In the present embodiment, a braid layer in which fine wires containing the same kind of material (stainless steel) as that of the reinforcement wire 24 are braided in a mesh shape is exemplified as the second reinforcement wire 42.

The wire diameter and the number of each of the second reinforcement wire 42 and the reinforcement wire 24 may be the same as or different from each other.

A first marker 14 and a second marker 16 which is positioned further toward the proximal side than this first marker 14 are provided at the distal portion DE of the sheath portion 10. The first marker 14 and the second marker 16 are ring-like members containing a material such as platinum through which radiation such as an X-ray is impermeable. Using the positions of the two markers of the first marker 14 and the second marker 16 as indicators, it is possible to visually check the position of the distal end of the sheath portion 10 in a lumen in a living body (blood vessel) during radiation (X-ray) observation. Accordingly, it is possible to easily determine the optimum timing for performing an operation of bending the catheter 100.

The distal portion of the operation wire 30 is fixed to a portion which is further toward the distal side than the second marker 16 in the sheath portion 10. By pulling the operation wire 30, the portion which is further toward the distal side than the second marker 16 in the distal portion DE is bent. In the catheter 100 of the present embodiment, the distal portion of the operation wire 30 is fixed to the first marker 14. The aspect of fixing the operation wire 30 to the first marker 14 is not particularly limited, and examples thereof include solder joining, thermal fusion, bonding using an adhesive, and mechanical locking between the operation wire 30 and the first marker 14.

The proximal sides of the wire-reinforced layer 26 and the second reinforced layer 40 are positioned up to the proximal end of the sheath portion 10, that is, positioned inside the operation portion 50.

The distal end of the inner layer 22 may reach the distal end of the sheath portion 10, or may be terminated further toward the slightly proximal side than the distal end of the sheath portion 10, that is, on the slightly inside. The proximal end of the inner layer 22 is positioned up to the proximal end of the sheath portion 10, that is, on the inside of the operation portion 50.

An example of a typical dimension of the sheath portion 10 will be described.

The diameter of the main lumen 20 is 400 µm to 600 µm (including an upper limit value and a lower limit value, and the same applies to the following), the thickness of the inner layer 22 is 5 µm to 30 µm, and the thickness of the outer layer 38 is 10 µm to 200 µm. The wall thickness of the hollow tube 28 is thinner than that of the inner layer 22, and is 1 µm to 10 µm. The inner diameter of the wire-reinforced layer 26 is 410 µm to 660 µm, the outer diameter of the wire-reinforced layer 26 is 450 µm to 740 µm, the inner diameter of the second reinforced layer 40 is 560 µm to 920 µm, and the outer diameter of the second reinforced layer 40 is 600 µm to 940 µm.

The inner diameter of the first marker 14 is 450 µm to 740 µm, the outer diameter of the first marker 14 is 490 µm to 820 µm, the inner diameter of the second marker 16 is 600 µm to 940 µm, and the outer diameter of the second marker 16 is 640 µm to 960 µm.

The radius (distance) from the shaft center of the catheter 100 to the center of the hollow tube 28 is 300 µm to 450 µm, the inner diameter (diameter) of the hollow tube 28 is 40 µm to 100 µm, and the thickness of the operation wire 30 is 25 µm to 60 µm.

The diameter of the sheath portion 10 is 700 µm to 980 nm, that is, the outer diameter is less than 1 mm, and the sheath portion 10 constitutes a micro-catheter which can be inserted into a peripheral blood vessel.

The linear expansion coefficient of the sheath portion 10 is larger than that of the operation wire 30. For example, the linear expansion coefficient of the sheath portion 10 is 100 ppm/K to 300 ppm/K, and the cell expansion coefficient of the operation wire 30 is 10 ppm/K to 30 ppm/K.

In addition, the swelling coefficient of the sheath portion 10 is larger than that of the operation wire 30. The linear expansion coefficient or the swelling coefficient of the sheath portion 10 is a linear expansion coefficient or a swelling coefficient when the whole stacked structure of the sheath portion 10 is viewed. That is, the linear expansion coefficient or the swelling coefficient of the sheath portion is a linear expansion coefficient or a swelling coefficient of a combined composite structure of components (excluding the operation wire 30) in which the inner layer 22, the outer layer 38, the wire-reinforced layer 26, the second reinforced layer 40, the hollow tube 28, and others are closely adhered to each other and integrated. The linear expansion coefficient or the swelling coefficient of the whole sheath portion can be estimated by multiplying each Young's modulus and the area ratio in the cross-sectional area by the single linear expansion coefficient or the swelling coefficient of each of the above-described components.

Inner Structure of Operation Portion 50

Next, the inner structure of the operation portion 50 will be described in detail.

FIG. 5 is a schematic plan view illustrating the inner structure of the operation portion 50.

FIG. 6 is an exploded schematic perspective view in which the lower main body 84 and the turning operation portion 60 in the present embodiment are viewed from above.

FIG. 7 is a schematic perspective view in which the engagement member 63 and the wire fixation panel 64 in the present embodiment are viewed from below.

FIG. 8A is a schematic plan view in which a state in which the engagement member 63 and the wire fixation panel 64 in the present embodiment are combined is viewed from above.

FIG. 8B is a cross-sectional view of line B-B in FIG. 8A.

FIG. 9A is a view showing a state in which the operation wire 30 is loosened in the wire fixation panel 64 and showing the moment when a turning operation is performed clockwise.

FIG. 9B is a schematic view showing the moment when a turning operation is performed counterclockwise.

As shown in FIG. 5, the proximal portion PE of the sheath portion 10 passes through the lower portion of the turning operation portion 60 and is drawn to more rearward than the rear end portion 84b of the operation portion main body 80 (lower main body 84). The proximal portion PE of the sheath portion 10 is bored with a side hole 12 from the outer peripheral surface of the sheath portion 10 to the hollow tube 28 at a position corresponding to the inside of the operation portion main body 80. The side hole 12 penetrates the peripheral surface of the hollow tube 28. The operation wires 30a and 30b are drawn from the inside of the hollow tube 28 to the outside through this side hole 12.

The proximal ends of the operation wires 30a and 30b drawn from the hollow tube 28 through the side hole 12 are fixed to the wire fixation panel 64 of the turning operation portion 60, and the operation wires are pulled by being wound through turning of the wire fixation panel 64.

More specifically, the wire fixation panel 64 has a plurality of engagement portions 66. The proximal ends of the operation wires 30a and 30b are respectively bound to predetermined engagement portions 66 and are then fixed using an adhesive. The method for binding the proximal ends of the operation wires with the engagement portions 66 can be arbitrarily selected. In addition, the operation wires 30a and 30b are wound around the wire fixation panel 64 over a winding angle exceeding an upper limit angle of the turning operation, in mutually opposite directions and are designed such that the operation wires 30 are sufficiently sent out even if the operation wires are subjected to a rotary operation up to the upper limit angle. The winding angle may mean an angle at which a state in which the operation wires 30 are wound around the wrapping portion 64c is checked from an upper direction.

In the present embodiment, more specifically, the upper limit angle of the turning operation is about 135 degrees. In addition, the wrapping angle of the operation wires 30a and 30b in an initial state exceeds 360 degrees but does not reach 720 degrees. In this manner, by setting a wrapping angle sufficiently exceeding the upper limit angle of the turning operation, loosening of the operation wires 30 is dispersed and the distance at which the operation wires 30 are separated from the wire fixation panel 64 is decreased.

As shown in FIG. 6, the turning operation portion 60 of the present embodiment includes the dial operation portion 61, a limiter member 62, the engagement member 63, the wire fixation panel 64, and the shaft member 65.

The dial operation portion 61 is disposed on an outer peripheral side of the turning operation portion 60 and is a rotation panel with which an operator directly comes into contact using a finger for operation.

The limiter member 62 is non-rotatably mounted on the dial operation portion 61. The limiter member 62 has a spring engagement portion 62a and a shaft portion 62b. The spring engagement portion 62a is an elastic deformation member which is deformed so as to be projected and retracted in a radial direction of the limiter member 62. A rotation shaft 65a of the shaft member 65 is inserted into the shaft portion 62b. A non-circular locking convex portion 62c is formed on an upper portion of the shaft portion 62b. The locking convex portion 62c is non-rotatably fitted to an opening portion 61c of the dial operation portion 61. Accordingly, the limiter member 62 and the dial operation portion 61 are integrally rotated around the rotation shaft 65a.

The engagement member 63 is an annular member through which the shaft portion 62b of the limiter member 62 is inserted and which is detachably engaged with the spring engagement portion 62a. The engagement member 63 forms a bottomed annular shape, and a waveform concavo-convex portion 63a is formed on the inner peripheral surface of a circular peripheral wall. The spring engagement portion 62a of the limiter member 62 is engaged at a plurality of portions of the concavo-convex portion 63a in the peripheral direction. When the limiter member 62 and the engagement member 63 are relatively twisted at a predetermined or more torque, the engagement between the spring engagement portion 62a and the concavo-convex portion 63a is released. The engagement member 63 has a plurality of recessed portions 63b.

The wire fixation panel 64 is a bobbin around which the operation wires 30a and 30b are wound. The wire fixation panel 64 includes a pair of flange portions 64b having a large diameter, and the wrapping portion 64c which is formed therebetween and has a small diameter. A plurality of engagement portions 66 are formed on an upper flange portion 64b. In FIG. 6, each engagement portion 66 is formed on both sides of two slits 64a.

A plurality of projection portions 64d are formed on the upper surface of the wire fixation panel 64. The engagement member 63 is non-rotatably fixed to the wire fixation panel 64 using the projection portions 64d fitted to the recessed portions 63b of the engagement member 63, and both of the engagement member and the wire fixation panel are rotatably and pivotally supported by the shaft member 65.

As described above, using the limiter member 62 and the engagement member 63 mutually twisted at a predetermined or more torque, the engagement between the spring engagement portion 62a of the limiter member 62 and the engagement member 63 are released. For this reason, even in a case where a user applies the above-described predetermined or more torque to the dial operation portion 61, this torque is not transmitted to the operation wire 30a or 30b through the engagement member 63 and the wire fixation panel 64. In other words, the limiter member 62 and the engagement member 63 constitute a pulling amount-limiting portion which operates according to a reaction force received from the operation wire 30 through a turning operation and limits the pulling of the operation wires 30a and 30b to be less than or equal to a predetermined amount.

In the present embodiment, a configuration example of the pulling amount-limiting portion which limits the torque (pulling force) to be less than or equal to a predetermined value has been shown. However, the pulling amount-limiting portion may be configured to limit the distance (pulling length) at which operation wires 30 are pulled to be less than or equal to a predetermined value.

As shown in FIG. 7 or 8, the wire fixation panel 64 (winding portion) includes the wrapping portion 64c (side peripheral surface); upper and lower flange portions 64b formed in the wrapping portion 64c; an opening portion 64e which is provided in the lower flange portion 64b, and a protrusion portion 64f. The penetration portion 63c (guard portion) of the engagement member 63 is a projection portion which is penetrated into the opening portion 64e. In addition, the wire fixation panel 64 (winding portion) includes a slit 64a (opening portion) in the upper flange portion 64b, and the penetration portion 63c and the closing portion 63d (guard portion) of the engagement member 63 is a projection portion which is penetrated into the slit 64a.

More specifically, in the wire fixation panel 64 (winding portion), the pair of flange portions 64b are formed so as to pinch the wrapping portion 64c (side peripheral surface), and the opening portion 64e and the slit 64a are provided in the pair of flange portions 64b so as to face each other. The penetration portion 63c of the engagement member 63 is provided from the slit 64a (one opening portion) over the opening portion 64e (the other opening portion) as a guard portion in a turning shaft direction of the wrapping portion 64c (side peripheral surface). In other words, the dimension in which the penetration portion 63c protrudes from the slit 64a is larger than the thickness of the wrapping portion 64c. As a result, the tip of the penetration portion 63c enters the opening portion 64e.

With such a configuration, in the wire fixation panel 64, it is possible to press the operation wires 30 into a region (refer to FIG. 8B) which is surrounded by the wrapping portion 64c, the flange portions 64b, and the guard portion (the penetration portion 63c and the closing portion 63d) of the engagement member 63, and thereby preventing deviation of the operation wires 30.

The operation wires 30 separated from the wrapping portion 64*c* through the turning operation are enlarged in a substantially circular shape.

It is necessary for the flange portions 64*b* to allow the loosening of the operation wires 30 to some extent in inner regions of the flange portions for a smooth turning operation. In contrast, it is necessary for the flange portions 64*b* to press the loosened operation wires 30 to the inner regions thereof in order to prevent the deviation of the operation wires 30.

For this reason, a circular shape or a shape similar to the circular shape is suitable for the shape of a flange portion 64*b*. Moreover, it is preferable that the guard portion be provided inside an inclusion circle which includes the flange portion 64*b* and comes into contact with the outer peripheral surface of the flange portion 64*b* around a rotation shaft of the wire fixation panel 64 (winding portion).

The inclusion circle virtually represents the limitation of the loosening of the operation wires 30 allowed by the flange portion 64*b*. In addition, the flange portion 64*b* in the present embodiment has a circular shape, and therefore, the outer peripheral surface of the flange portion 64*b* is equal to the inclusion circle.

The provision of the guard portion inside the inclusion circle means that at least a part of the guard portion may be disposed inside the inclusion circle. However, it is more preferable that the entirety of the guard portion be disposed inside the inclusion circle. Based on the present embodiment, it is preferable that each of the penetration portion 63*c* and the closing portion 63*d* of the engagement member 63 as the guard portion be disposed inside the inclusion circle.

As described above, the turning operation portion 60 has the engagement member 63 (fitting portion) which is fitted to the wire fixation panel 64 (winding portion) in the turning shaft direction of the wire fixation panel 64. In addition, as shown in the drawing, the penetration portion 63*c* and the closing portion 63*d* (guard portion) are disposed at a position facing the operation wires 30 wound around the wrapping portion 64*c* due to the fitting of the engagement member 63 to the wire fixation panel 64, and can be turned integrally with the wire fixation panel 64.

The "fitting" refers to a state in which either of the engagement member 63 or the wire fixation panel 64 is inserted inside the other or a state in which either of the engagement member or the wire fixation panel is mounted on the outside of the other.

As previously described, the wire fixation panel 64 and the guard portion (the penetration portion 63*c* and the closing portion 63*d*) are constituted of different members. For this reason, it is possible to attach the guard portion to the wire fixation panel 64 (wrapping portion 64*c*) after winding the operation wires 30 thereto. With such a configuration, it is possible to easily perform the wrapping work of the operation wires 30. Therefore, such a configuration is particularly suitable for the catheter 100 of which the winding angle of an operation wire 30 in the initial state exceeds 360 degrees as in the present embodiment.

In addition, using the simple work of fitting the engagement member 63 to the wire fixation panel 64 in the shaft direction, it is possible to attach the guard portion to a desired position and to maintain the fitted state.

The penetration portion 63*c* in the present embodiment is formed such that one projection portion penetrates the opening portion 64*e* from the slit 64*a*, but the present invention is not necessarily limited to this aspect. For example, an aspect is possible in which a projection portion protruding from the slit 64*a* and a projection portion protruding from the opening portion 64*e* are disposed so as to overlap each other when viewed from the turning center and these projection portions function similarly to the penetration portion 63*c* of the present embodiment.

In addition, the wrapping portion 64*c*, the flange portion 64*b*, and the penetration portion 63*c* in the present embodiment are constituted so as to surround all directions around the operation wire 30 when viewed as, for example, a cross section. However, the present invention is not limited to necessarily surround all directions, and there may be a gap in a partial direction. Accordingly, the dimension in which the penetration portion 63*c* protrudes from the slit 64*a* may be smaller than the width of the wrapping portion 64*c*.

The position of the penetration portion 63*c* can be arbitrarily set as long as it is possible to achieve the purpose. In the initial state shown in FIG. 5, when a straight line is drawn on the operation wire 30 which is drawn to the side hole 12 of the sheath portion 10 from a contact/separation point while passing through the contact/separation point at which the operation wire 30 comes into contact with and is separated from the wrapping portion 64*c* when seen from the upper direction, it is preferable that the penetration portion 63*c* be provided outside the straight line in the width direction of the operation portion 50 and/or in a region facing the operation wire 30 (operation wire 30 on the engagement portion 66 side which is a fixed end in the turning operation portion 60) further toward a proximal side than the contact/separation point in the initial state. With such a disposition, the penetration portion 63*c* can catch the operation wire 30 through movement of the penetration portion 63*c* so as to run after the operation wire 30 which has been loosened once by being sent through a turning operation. In the turning operation after the operation wire 30 is caught, the drawing path of the operation wire 30 is changed by the movement of the penetration portion 63*c*, thereby suppressing the loosening caused in the operation wire 30.

The position of the penetration portion 63*c* may be changed depending on the wrapping angle of the operation wire to be selected.

The slit 64*a* (notch) is formed in the wire fixation panel 64 (winding portion) as an opening portion inward from the outer peripheral side of the flange portion 64*b*. The operation wire 30 drawn from the slit 64*a* is fixed to the engagement portion 66 of the wire fixation panel 64. The closing portion 63*d* (guard portion) closes an outer peripheral side than the wrapping portion 64*c* in the slit 64*a*.

The slit 64*a* which has been provided in order to draw the operation wire 30 to the engagement portion 66 is one portion in which the operation wire 30 can easily deviate from the wire fixation panel 64. Accordingly, the position at which the closing portion 63*d* is to be provided is preferably the slit 64*a*.

The penetration portion 63*c* of the engagement member 63 of the present embodiment is provided from the slit 64*a* (notch) of a pair of flange portions 64*b* over the opening portion 64*e* (another opening portion), and the closing portion 63*d* of the engagement member 63 closes an outer peripheral side than the position of the penetration portion 63*c* in the slit 64*a*. The gap between the slit 64*a* and the closing portion 63*d* is smaller than the diameter dimension of the operation wire 30. Accordingly, it is possible to more reliably prevent the operation wire 30 from deviating from the slit 64*a*.

As shown in FIG. 7 or FIGS. 8A and 8B, the penetration portion 63*c* and the closing portion 63*d* are integrally formed in the present embodiment. However, the present invention is not limited to this aspect, and an aspect in which a gap between the penetration portion 63c and the closing portion 63d is provided may be used.

A plurality of slits 64a (notches) are formed in the flange portion 64b. The number of slits can be arbitrarily set. A pair of operation wires 30a and 30b are fixed to the wire fixation panel 64 by being respectively drawn from different slits 64a. The penetration portion 63c and the closing portion 63d (guard portion) are formed with respect to each of the plurality of slits 64a from which the operation wires 30a and 30b are drawn.

That is, a slit 64a and engagement portions 66 for pulling are provided in the wire fixation panel 64 for each of the operation wires 30a and 30b and prevent the operation wires 30a and 30b from being tangled in the vicinity of the engagement portions 66. By providing the penetration portion 63c and the closing portion 63d for each slit 64a, it is possible to prevent the operation wires 30a and 30b from respectively deviating from the slits 64a.

As shown in FIG. 5 or 6, the shaft member 65 is a holding member having a circular recessed portion which accommodates the wire fixation panel 64, and includes the rotation shaft 65a protruding upward; and guide ribs 65b and 65c respectively protruding downward. The penetration portion 63c and the closing portion 63d (guard portion) of the engagement member 63 are preferably disposed in an inner space included in the shaft member 65 which accommodates the wire fixation panel 64 as in the present embodiment. This is because the shaft member 65 is a member which accommodates the wire fixation panel 64 functioning as a winding portion of the present embodiment, and an object of the present invention is to prevent the operation wires 30 from deviating from the winding portion.

The dial operation portion 61, the limiter member 62, the engagement member 63, and the wire fixation panel 64 are rotatably mounted on the rotation shaft 65a. Accordingly, the turning operation portion 60 is integrally constituted.

The guide ribs 65b and 65c are two pairs of parallel plate-like projection portions. A claw portion 68 protruding outward is formed in each pair of guide ribs 65cb.

In addition, the shaft member 65 has a guide groove 65d (refer to FIG. 6) which is a circular arc-like groove on the upper portion, and the guide groove 65d is formed such that the protrusion portion 64f (refer to FIG. 7) provided below the wire fixation panel 64 is accommodated. That is, the guide groove 65d and the protrusion portion 64f constitute angle-restricting mechanisms which are engaged with each other due to a turning operation reaching a predetermined rotation angle and restrict the turning operation.

In the present embodiment, when the turning operation reaches about 135 degrees, the protrusion portion 64f abuts on an end portion of the guide groove 65d and the turning operation is restricted.

In a case where it is possible to perform a turning operation exceeding an upper limit angle in the configuration of the present embodiment, the penetration portion 63c comes into contact with the operation wire 30 on a pulled side and applies excess tension. Therefore, the operation wire 30 is easily broken. The angle-restricting mechanisms in the present embodiment can prevent such breakage of the operation wire 30.

The protrusion portion 64f and the guide groove 65d of the present embodiment show an example of the angle-restricting mechanisms, although another aspect may be used to realize the angle-restricting mechanisms.

The lower main body 84 includes an inner guide 84j which comes into contact with the guide rib 65b; and an intermittent rib 84i which comes into contact with the guide rib 65c. The inner guide 84j and the intermittent rib 84i are a pair of plate-like protruding portions respectively extending in forward and backward directions of the lower main body 84. A pair of intermittent ribs 84i are an aggregation of a plurality of rib pieces which are discretely formed by being divided by a gap 84h.

When the shaft member 65 is mounted on the lower main body 84, the claw portion 68 is engaged with the gap 84h, the guide ribs 65c are disposed along the inside of the pair of intermittent ribs 84i, and the guide ribs 65b are disposed by being interposed between the inner guides 84j and the intermittent ribs 84i.

In the above-described configuration, the turning operation portion 60, which is formed by integrally combining the dial operation portion 61, the limiter member 62, the engagement member 63, the wire fixation panel 64, and the shaft member 65, is attached and fixed to the lower main body 84.

<Turning Operation and Loosening Caused in Operation Wire 30>

FIGS. 9A and 9B are views showing states in which the operation wires 30 are loosened in the wire fixation panel 64. FIG. 9A is a view showing a state in which a turning operation is performed clockwise and the turning angle has reached an upper limit angle (about 135 degrees in the present embodiment). FIG. 9B is a view showing a state in which a turning operation is performed counterclockwise and the turning angle has reached the upper limit angle.

As shown in FIG. 9A, in a case where a turning operation is performed clockwise from the initial state shown in FIG. 5, the operation wire 30a which has been pulled enters a tensed state and the operation wire 30b which has been sent out enters a relaxed state. When the turning operation reaches a predetermined angle, the penetration portion 63c abuts on the operation wire 30b (the other operation wire) which has been sent out through the turning operation, and the operation wire 30b is pulled in the rotation direction of the turning operation through the turning operation further exceeding the predetermined angle.

The shaft member 65 is not rotated whereas the wire fixation panel 64 is rotated through the turning operation. Therefore, it is difficult to make the shaft member and the wire fixation panel be closely adhered to each other, and it is necessary to provide a small gap. If there is no penetration portion 63c, the operation wire 30b which has been loosened can deviate from the gap. However, in the present embodiment, the operation wire 30b is loosened once through the turning operation, and then the operation wire 30b is caught by the penetration portion 63c which has been moved and penetrates the slit 64a which is a drawing source of the operation wire 30a, and is pulled to the operation wire 30a side by the penetration portion 63c. Accordingly, the drawing path of the operation wire 30b is changed and the loosening caused in the operation wire 30b is absorbed. Therefore, the operation wire 30b does not deviate from the gap.

In addition, the penetration portion 63c is provided integrally with the wire fixation panel 64. Therefore, when the rotation angle (sending amount of the operation wire 30b) of the wire fixation panel 64 is increased, the movement distance of the penetration portion 63c is increased, and thus, the variation degree of the drawing path of the operation wire 30b is also increased. That is, even if the rotation angle of the turning operation is increased, the penetration portion 63c can sufficiently suppress the loosening caused in the operation wire 30b.

In a case where the turning operation is performed counterclockwise as shown in FIG. 9B, the operation wire 30b is pulled and the operation wire 30a once enters a relaxed state. The reason the operation wire 30a which has entered the relaxed state does not deviate from the gap between the wire fixation panel 64 and the shaft member 65 is the same as the above-described reason the operation wire 30b does not deviate.

In addition, the closing portion 63d is disposed so as to close an outer peripheral side than the penetration portion 63c. Therefore, it is possible to prevent a defect in which the catheter 100 is not returned to the initial state due to the operation wire 30, which has been abut on the penetration portion 63c and is curved, being caught by the corner of the slit 64a.

In addition, if the turning operation is performed until the turning angle reaches the upper limit angle as shown in FIG. 9A or 9B, the operation wire 30 on a pulled side and the penetration portion 63c come into contact with each other. However, the rotation is not performed more than that, and therefore, excess tension is not applied to the operation wire 30.

In the present embodiment, the drawing has been shown such that the penetration portion 63c abuts on the operation wire 30 on a pulled side in addition to the operation wire 30 on a loosened side, when the turning operation is performed up to an upper limit angle of the angle-restricting mechanisms constituted of the protrusion portion 64f and the guide groove 65d. However, the upper limit angle may be appropriately set and the turning operation may not be necessarily performed until the penetration portion 63c abuts on the operation wire 30 on the pulled side.

The angle-restricting mechanisms are provided in the present embodiment, but are not necessarily provided. Even in a case of an aspect in which the angle-restricting mechanisms are not provided, the catheter 100 includes the limiter member 62 and the engagement member 63 (pulling amount-limiting portion), and therefore, predetermined or more tension is not applied to the operation wire 30.

More specifically, in a case where the turning operation is performed clockwise, a reaction force which the engagement member 63 receives from the operation wire 30a due to the turning operation is imparted counterclockwise (in a direction opposite to that of the turning operation). In addition, after the penetration portion 63c pulls the operation wire 30b until the operation wire 30b enters a tensed state in the case where the turning operation is performed clockwise, a reaction force which the engagement member 63 receives from the operation wire 30b due to the turning operation is applied clockwise (in the same direction as that of the turning operation) in the engagement portion 66 fixing the operation wire 30b and is applied counterclockwise (in a direction opposite to that of the turning operation) in the penetration portion 63c catching the operation wire 30b. At this time, the reaction force in the engagement portion 66 is a clockwise vector in a tangential direction in the outer peripheral surface of the wrapping portion 64c. In contrast, the reaction force in the penetration portion 63c acts on the engagement member 63 as a counterclockwise force such that vectors (a ($\alpha$) vector facing the side hole 12 of the sheath portion by having a contact point between the penetration portion 63c and the operation wire 30b as a starting point and a ($\beta$) vector facing a position (contact/separation point) at which the operation wire 30b comes into contact with and is separated from the wrapping portion 64c by having the contact point between the penetration portion 63c and the operation wire 30b as a starting point) in two directions are synthesized. In addition, as the rotation angle of the turning operation is increased, the angle formed by the ($\alpha$) vector and the ($\beta$) vector becomes an acute angle, and the magnitude of the added-up vectors (synthesis force) is gradually increased. With such an action, the synthesis force (counterclockwise reaction force) becomes larger than the reaction force (clockwise reaction force) in the engagement portion 66, and when the whole reaction force which the engagement member 63 receives from the operation wire 30b is synthesized, the synthesis force provides a counterclockwise vector.

As described above, the limiter member 62 and the engagement member 63 constitute the pulling amount-limiting portion which acts in accordance with a reaction force received from the operation wire 30 due to a turning operation and limits the pulling amount of the operation wire 30 to be less than or equal to a predetermined value. In addition, as shown in the above-described description, a reaction force which the engagement member 63 (turning operation portion) receives from the operation wire 30a (one operation wire) due to the turning operation and a reaction force which the engagement member 63 receives from the operation wire 30b (the other operation wire) which has entered a tensed state by being pulled in the rotation direction (clockwise) due to the turning operation are imparted in the same direction (counterclockwise). Accordingly, when a synthesis force of tension of the operation wire 30a and tension of the operation wire 30b becomes a predetermined value or more, the engagement between the limiter member 62 and the engagement member 63 is released. Accordingly, the limiter member 62 and the engagement member 63 can prevent application of predetermined or more tension to both of the operation wire 30a and the operation wire 30b.

In the description herein, the case when the turning operation is performed clockwise has been described. However, even in the case when the turning operation is performed counterclockwise, the limiter member 62 and the engagement member 63 prevent tension of the operation wire 30a and the operation wire 30b from being a predetermined value or more.

Second Embodiment

Next, a catheter 100 in a second embodiment of the present embodiment will be described.

Figure 10:
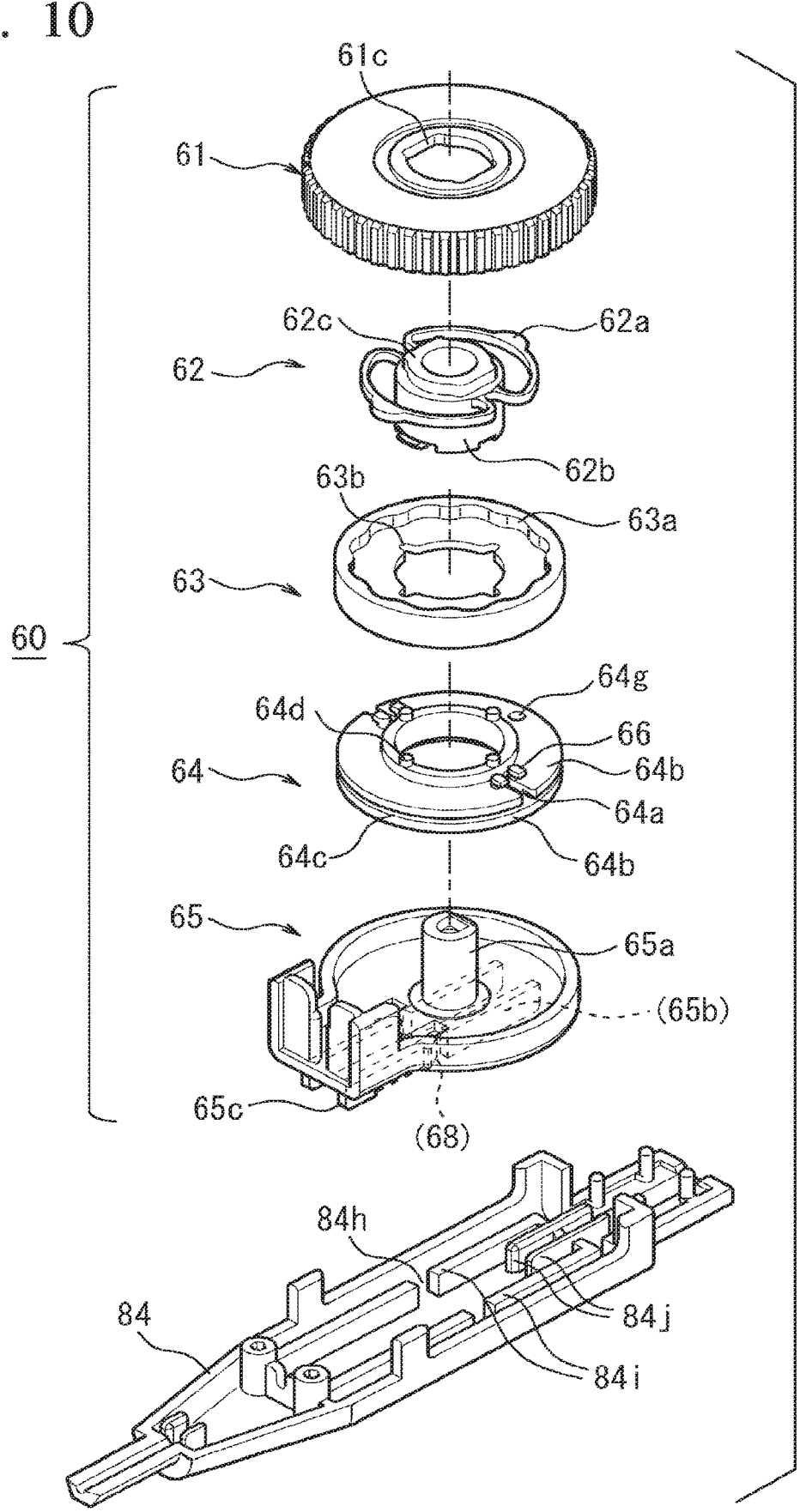
FIG. 10 is an exploded schematic perspective view from which several upper parts are excluded from a catheter showing a preferred example of a second embodiment of the present invention and in which a lower main body thereof and an exploded turning operation portion are viewed from above.

FIG. 10 is an exploded schematic perspective view in which a lower main body 84 and a turning operation portion 60 in the second embodiment are viewed from above.

Figure 11:
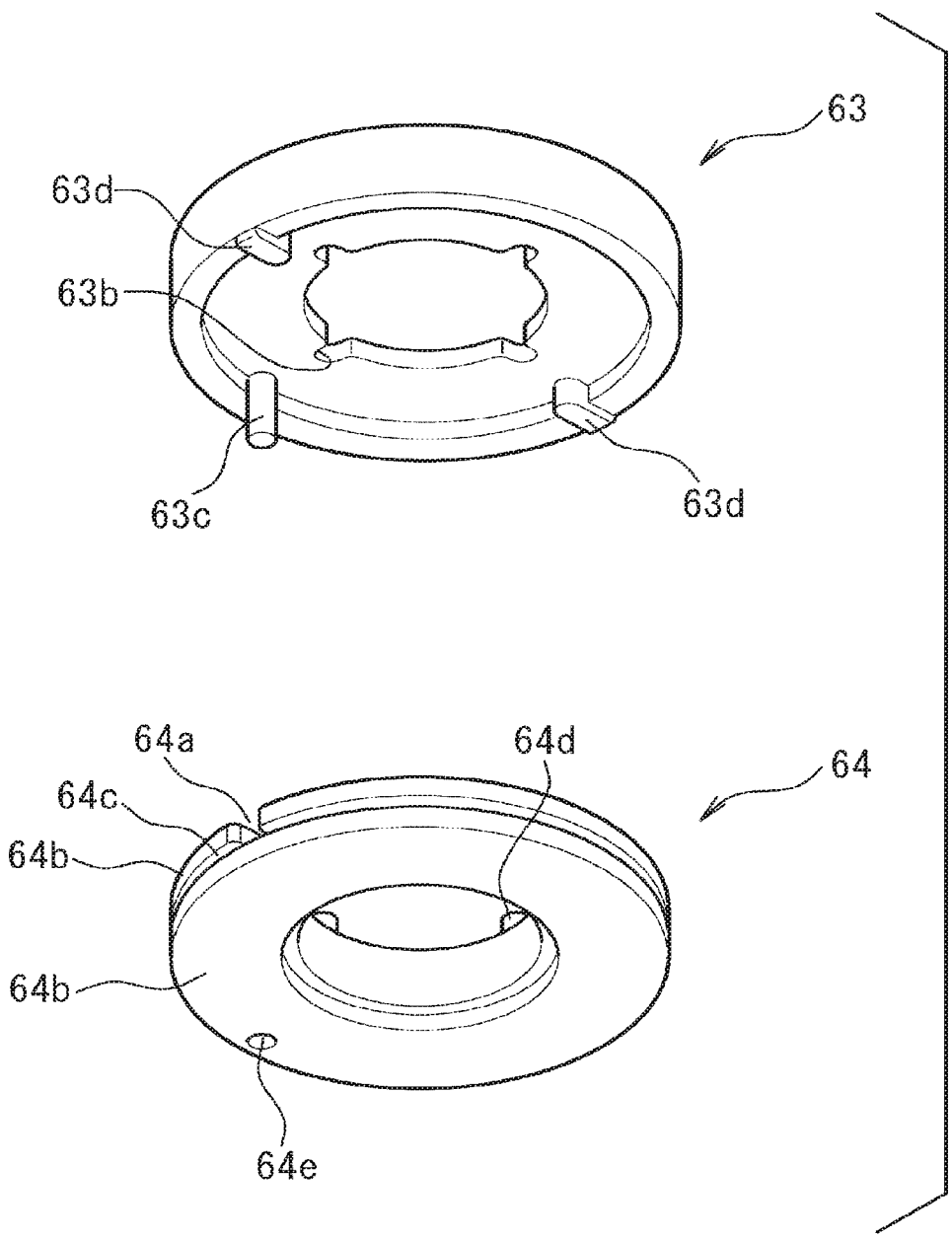
FIG. 11 is a schematic perspective view of the catheter shown in FIG. 10 in which an engagement member and a wire fixation panel are viewed from below.

FIG. 11 is a schematic perspective view in which an engagement member 63 and a wire fixation panel 64 in the second embodiment are viewed from below.

Figure 12A:
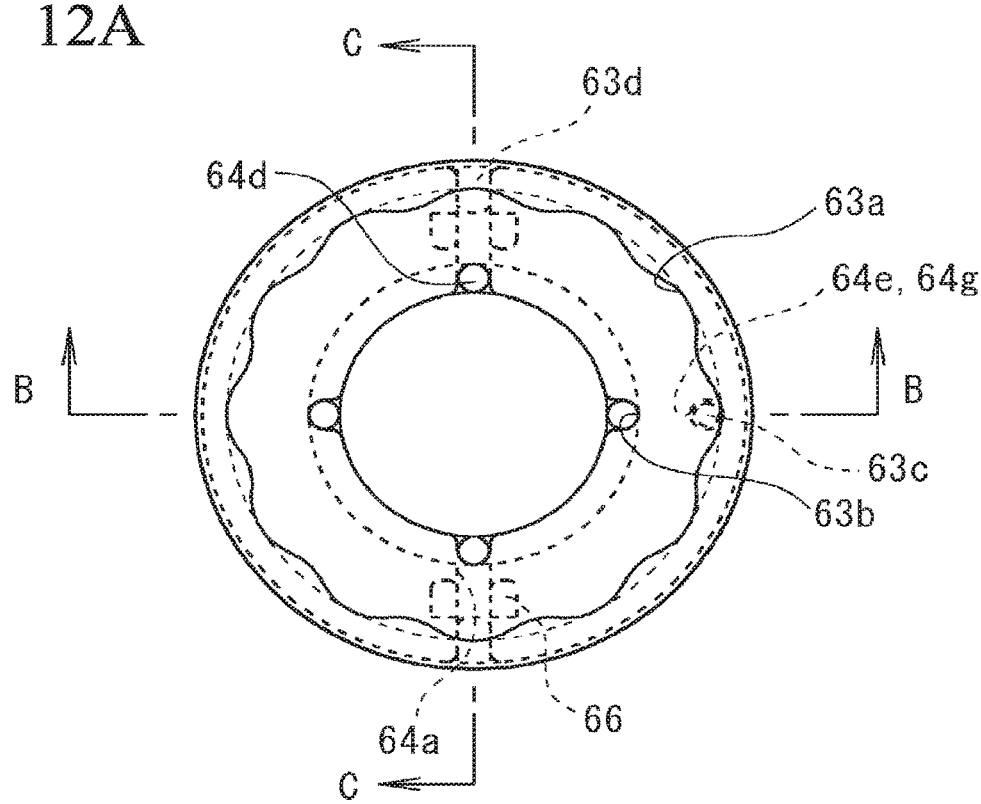
FIG. 12A is a schematic plan view in which a state in which the engagement member and the wire fixation panel shown in FIG. 11 are combined is viewed from above.
Figure 12B:
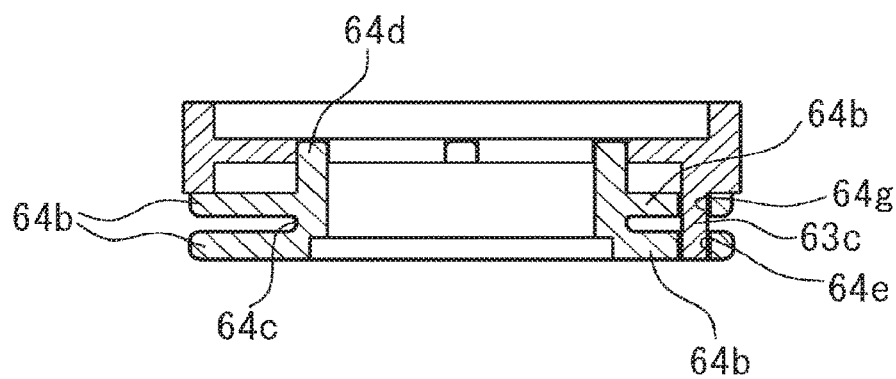
FIG. 12B is a cross-sectional view of line B-B of the combination of the engagement member and the wire fixation panel shown in FIG. 12A.
Figure 12C:
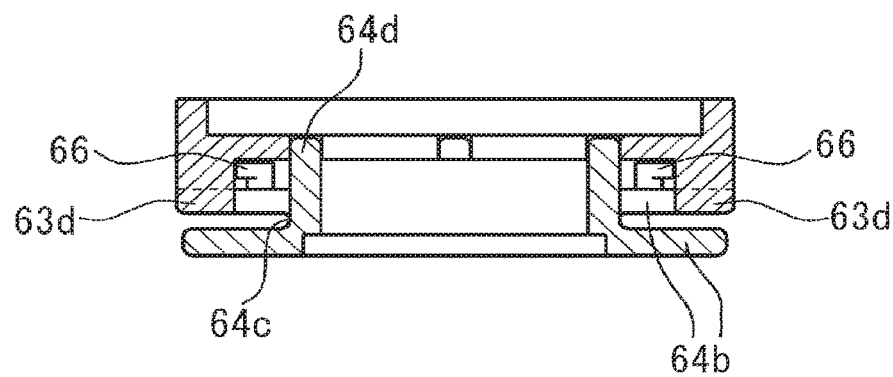
FIG. 12C is a cross-sectional view of line C-C of the combination of the engagement member and the wire fixation panel shown in FIG. 12A.

FIG. 12A is a schematic plan view in which a state in which the engagement member 63 and the wire fixation panel 64 in the second embodiment are combined is viewed from above. FIG. 12B is a cross-sectional view of line B-B of FIG. 12A. FIG. 12C is a cross-sectional view of line C-C of FIG. 12A.

The engagement member 63, the wire fixation panel 64, and the shaft member 65 in the first embodiment and the engagement member 63, the wire fixation panel 64, and a shaft member 65 in the second embodiment respectively have configurations different from each other. However, the same name is given to a component having the same function for convenience of description. In addition, members excluding the engagement member 63, the wire fixation panel 64, and the shaft member 65 are common in the first embodiment and the second embodiment, and therefore, the description thereof will not be repeated below.

A slit 64a (notch) is formed in the wire fixation panel 64 (winding portion) in the present embodiment as an opening portion inward from the outer peripheral side of a flange portion 64b, and operation wires 30a and 30b which are drawn from the slit 64a are fixed to the wire fixation panel. Using a separation point at which the operation wires 30 are separated from a wrapping portion 64c (side peripheral surface) as a reference in an initial state, opening portions 64e and 64g which are different from the slit 64a and face each other are formed in a flange portion 64b on a side opposite to a direction in which the operation wires 30 are drawn from the separation point to a sheath portion 10. A penetration portion 63c penetrates these opening portions 64e and 64g.

The initial state herein refers to a state at a point in time of shipment of the catheter 100 or at a point in time of starting use of the catheter.

In the present embodiment, there are separation points for respective operation wires 30a and 30b, and the penetration portion 63c is formed at a position on a side opposite to a direction in which the operation wire 30a is drawn and on a side opposite to a direction in which the operation wire 30b is drawn. More specifically, the penetration portion 63c is formed further toward a proximal side than the center of a turning operation, that is, on a rear end side on a center shaft of the sheath portion 10 in the initial state.

In addition, the separation points of the operation wires 30 in the initial state and the direction in which the operation wires 30 are drawn from the separation points to the sheath portion 10 in the present embodiment are the same as those in the first embodiment shown in FIG. 5.

With such a configuration, the rotation angle of a turning operation which is required for the penetration portion 63c to abut on the operation wire 30 on a sent out side through the turning operation is increased by about 90 degrees compared to that in the first embodiment. In addition, the rotation angle of a turning operation which is required for the penetration portion 63c to abut on the operation wire 30 on a pulled side through the turning operation is also increased by about 90 degrees compared to that in the first embodiment. Accordingly, the turning angle until an engagement, between a spring engagement portion 62a and a concavo-convex portion 63a is released is increased compared to that in the first embodiment. In other words, even in an aspect in which there is no function of restricting tension applied to the operation wires 30, an operation of bending the catheter 100 constituted of the limiter member 62 and the engagement member 63 can be performed using a large rotation angle.

As shown in FIGS. 10 and 11, in the present embodiment, there is neither a guide groove 65d nor a protrusion portion 64f of the first embodiment. That is, the catheter 100 of the present embodiment is different from the first embodiment in that there is no angle-restricting mechanism.

However, provision of the angle restricting mechanism may be provided. That is, in the catheter 100 in the present embodiment any angle-restricting mechanism may be provided.

A closing portion 63d (guard portion) closes the slit 64a (notch), and the gap between the slit 64a and the closing portion 63d is preferably smaller than the diameter dimension of the operation wire 30.

That is, the present embodiment is different from the first embodiment in that the penetration portion 63c and the closing portion 63d of the catheter 100 of the present embodiment are formed so as to be disposed at a position different from each other whereas the penetration portion 63c and the closing portion 63d of the catheter 100 of the first embodiment are integrally formed.

In addition, the present embodiment is different from the first embodiment in that the penetration portion 63c in the present embodiment penetrates the opening portion 64e which is provided in the lower flange portion 64b from the opening portion 64g which is provided in the lower flange portion 64b whereas the penetration portion 63c in the first embodiment penetrates the opening portion 64e from the slit 64a.

Accordingly, it is possible to prevent the operation wire 30 from being caught by the corner of the slit 64a or deviating from the slit 64a.

As shown in FIG. 12C, the dimension (length) in which the closing portion 63d in the present embodiment penetrates the flange portion 64b is preferably less than or equal to the thickness of the flange portion 64b. This is because there is a concern that the operation wire 30 may be caught by the closing portion 63d through a turning operation and the closing portion 63d unexpectedly applies tension to the operation wire 30, in a case where the dimension exceeds the thickness of the flange portion 64b.

Third Embodiment

Next, a catheter 100 in a third embodiment of the present embodiment will be described.

Figure 13:
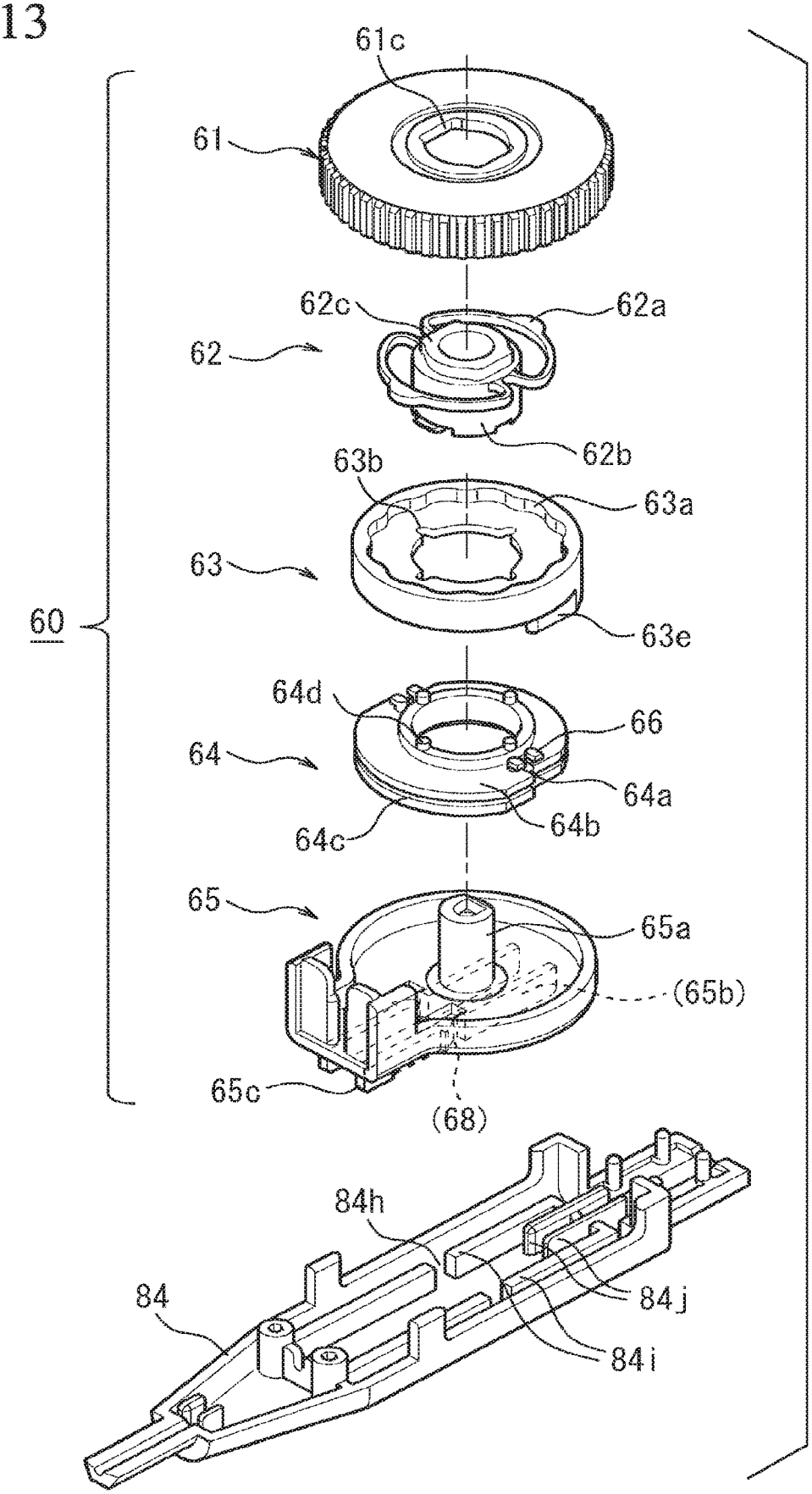
FIG. 13 is an exploded schematic perspective view from which several upper parts are excluded from a catheter showing a preferred example of a third embodiment of the present invention and in which a lower main body thereof and an exploded turning operation portion are viewed from above.

FIG. 13 is an exploded schematic perspective view in which a lower main body 84 and a turning operation portion 60 in the third embodiment are viewed from above.

Figure 14:
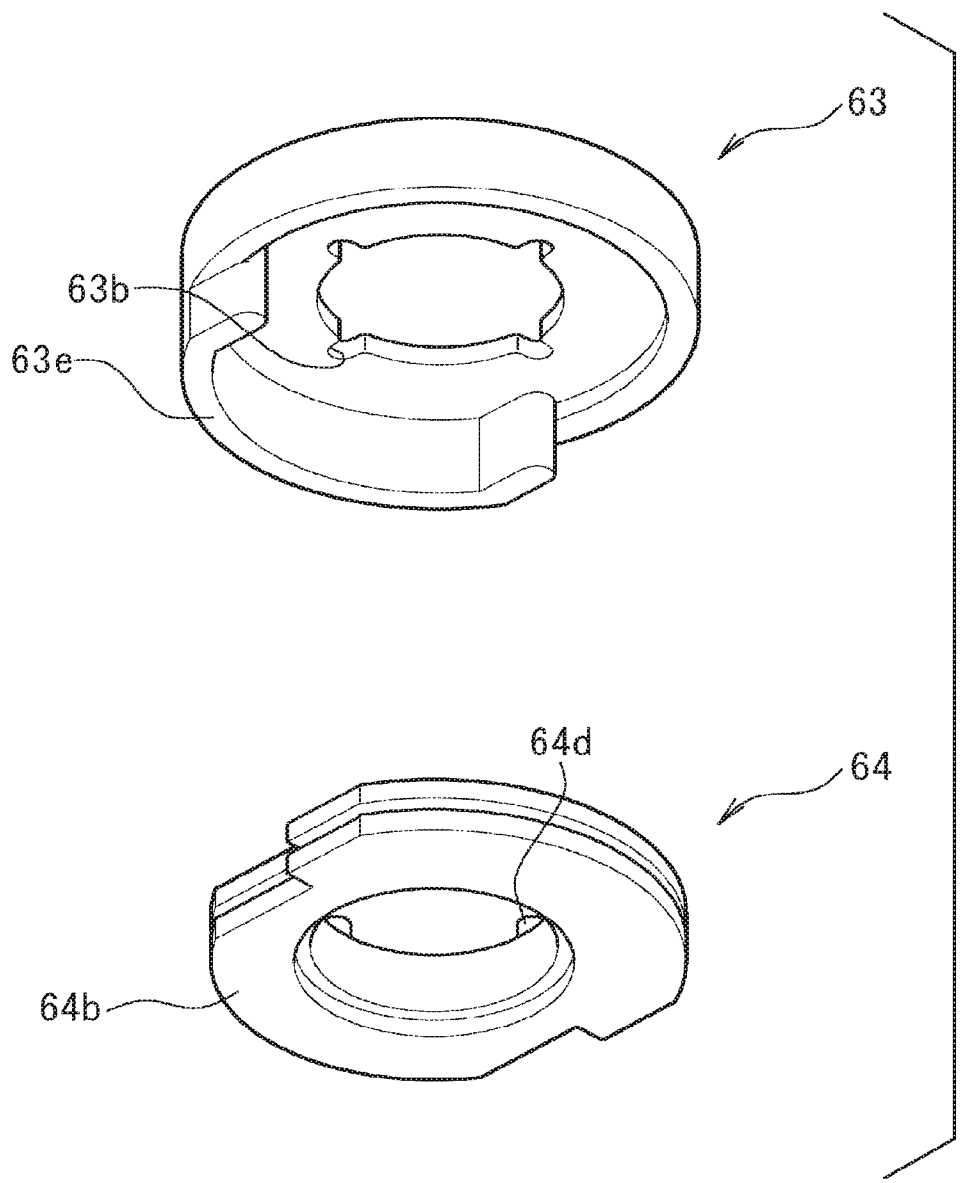
FIG. 14 is a schematic perspective view of the catheter shown in FIG. 13 in which an engagement member and a wire fixation panel are viewed from below.

FIG. 14 is a schematic perspective view in which an engagement member 63 and a wire fixation panel 64 in the third embodiment are viewed from below.

Figure 15A:
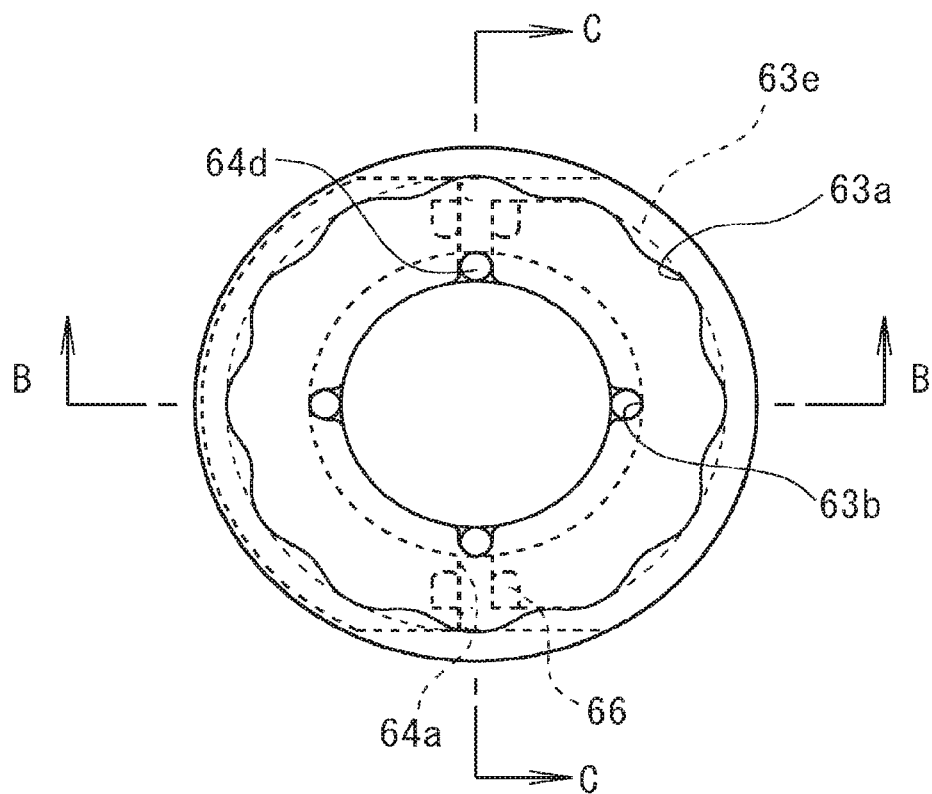
FIG. 15A is a schematic plan view in which a state in which the engagement member and the wire fixation panel shown in FIG. 14 are combined is viewed from above.
Figure 15B:
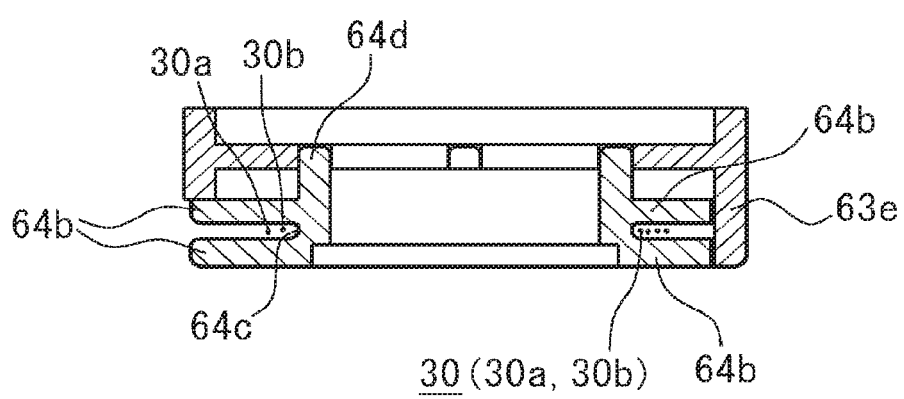
FIG. 15B is a cross-sectional view of line B-B of the combination of the engagement member and the wire fixation panel shown in FIG. 15A.
Figure 15C:
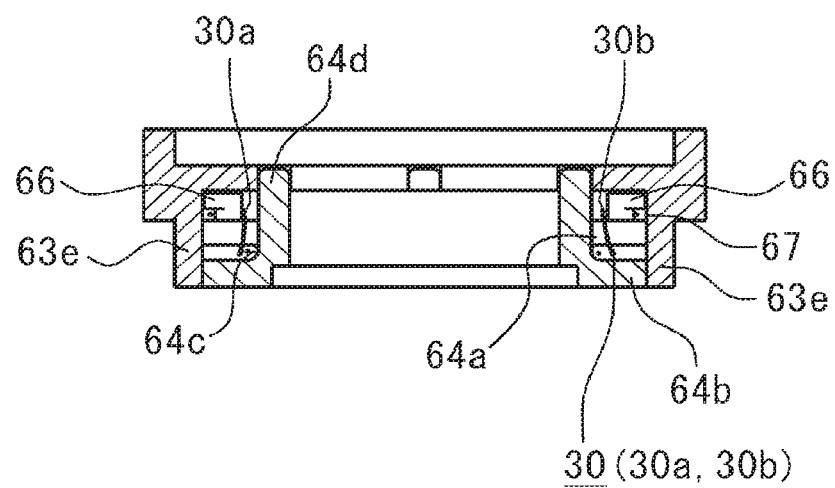
FIG. 15C is a cross-sectional view of line C-C of the combination of the engagement member and the wire fixation panel shown in FIG. 15A.

FIG. 15A is a schematic plan view in which a state in which the engagement member 63 and the wire fixation panel 64 in the third embodiment are combined is viewed from above. FIG. 15B is a cross-sectional view of line B-B in FIG. 15A. FIG. 15C is a cross-sectional view of line C-C in FIG. 15A.

The engagement member 63 and the wire fixation panel 64 in the second embodiment and the engagement member 63 and the wire fixation panel 64 in the third embodiment respectively have configurations different from each other. However, the same name is given to a component having the same function for convenience of description. In addition, members excluding the engagement member 63 and the wire fixation panel 64 are common in the second embodiment and the third embodiment, and therefore, the description thereof will not be repeated below.

In addition, operation wires 30 (30a and 30b) are not shown in FIG. 15A. However, the operation wires 30 are schematically shown in FIGS. 15B and 15C. The diameter dimensions of the operation wires 30 shown in FIGS. 15B and 15C are enlarged in order to ease visual recognition, and the dimension ratio with other portions is not accurate.

The guard portions (the penetration portion 63c or the closing portion 63d) of the above-described other embodiments are projection portions which are projected in a pin shape. In contrast, a guard portion 63e of the present embodiment is different therefrom in that the guard portion of the present embodiment extends by being biased to one side and has a curved plate shape as shown in FIG. 14.

In addition, the flange portion 64b of the present embodiment has a distorted shape as shown in FIG. 14, when a side facing the guard portion 63e and on an opposite side are observed. That is, the flange portion of the present embodiment is different from the flange portions 64b of the above-described other embodiments in that the flange portion does not have the same shape on the side facing the guard portion and on the opposite side.

More specifically, using a separation point at which the operation wires 30 are separated from a wrapping portion 64c (side peripheral surface) as a reference in an initial state, the guard portion 63e extends by being biased to a side opposite to the direction in which the operation wires 30 are drawn from the separation point to a sheath portion 10.

In this manner, the guard portion 63e is provided by being biased to a side on which loosening of the operation wires 30 is easily caused when a turning operation is started. Therefore, an effect of preventing the loosening of the operation wires 30 is sufficiently exhibited from the start of the operation.

In addition, similarly to the other embodiments, in the present embodiment, the operation wires 30 are wound around the wrapping portion 64c (side peripheral surface) over a winding angle which exceeds 360 degrees but does not reach 720 degrees in the initial state. When considering the winding of the operation wires 30, the extension direction of the guard portion 63e can also be explained as below. That is, the guard portion 63e extends by being biased to a side on which the winding using the same operation wire 30 is more overlapping, that is, a side on which there are many turns of the wire.

As shown in FIG. 15B, winding of any of the operation wires 30 (30a and 30b) of the present embodiment is overlapping on the proximal side, that is, on the rear end side, and the operation wires 30 (30a and 30b) are singly wound on the distal side. There is no guard portion 63e in the distal side whereas the guard portion 63e extends to the proximal side.

In addition, similarly to the other embodiments, in the present embodiment, a pair of engagement portions 66 (fixation portions) in which proximal sides of a pair of operation wires 30 are individually fixed to the wire fixation panel 64 (winding portion) are formed. When considering the positions of these engagement portions 66, the extension direction of the guard portion 63e can also be explained as below. That is, the guard portion 63e rotates from one engagement portion 66 to the other engagement portion 66.

More specifically, a pair of slits 64a (notches) are inwardly formed in the vicinity of the engagement portions 66 from the outer peripheral side of the flange portions 64b, and the operation wires 30 are drawn therefrom. The guard portion 63e rotates from one slit 64a to the other slit 64a.

In this manner, the guard portion 63e is continuously provided, and therefore, it is possible to improve the effect of preventing loosening of the operation wires 30. In addition, the guard portion 63e is provided in the slits 64a, and therefore, it is also possible to prevent deviation of the operation wires 30 from the slits 64a.

Compared to the flange portions 64b in the other embodiments, the flange portion 64b in the present embodiment has a notched form according to a region in which the guard portion 63e extends, and has a shape biased to a side opposite to a side facing the guard portion 63e.

The flange portion 64b is covered with the guard portion 63e in a state in which the engagement member 63 is fitted to the wire fixation panel 64. In other words, the engagement member 63 which is formed in a tubular shape having a partial missing part covers a part of the wire fixation panel 64.

In a case where an inclusion circle (not shown in the drawing) which includes the flange portion 64b and comes into contact with the outer peripheral surface of the flange portion 64b around a rotation shaft of the wire fixation panel 64 is virtually provided, it is desirable to provide the guard portion 63e inside the inclusion circle.

The provision of the guard portion 63e inside the inclusion circle means that at least the inner peripheral surface of the guard portion 63e may be disposed inside the inclusion circle. However, more preferably, the outer peripheral surface of the guard portion 63e may also be disposed inside the inclusion circle.

In addition, a characteristic of the present embodiment is that the distance from the inner peripheral surface of the guard portion 63e to the wrapping portion 64c (side peripheral surface) is made shorter than that of other portions in the vicinity of the engagement portion 66 (fixation portion).

More specifically, as shown in FIG. 15C, the wire fixation panel 64 (winding portion) has the pair of flange portions 64b which are formed so as to pinch the wrapping portion 64c; and the slit 64a (notch) which is formed inward from the outer peripheral side in an upper flange portion 64b (one flange portion). Moreover, the engagement portion 66 is formed on one surface of the upper flange portion 64b on a side opposite to the surface facing the lower (the other flange portion). The operation wires 30 (30a and 30b) wound around the wrapping portion 64c are bound to the engagement portion 66 by being drawn from the slit 64a. Furthermore, the guard portion 63e faces the operation wire 30 wound around the wrapping portion 64c and also faces the operation wire 30 bound to the engagement portion 66.

The proximal side of the operation wire 30 is bound to the engagement portion 66. Therefore, the loosening of the operation wire 30 is easily complicated compared to other portions. In addition, the slit 64a is formed in the vicinity of the engagement portion 66, and therefore, in some cases, a defect in which the operation wire 30 is caught by the corner of the slit 64a may be caused. The guard portion 63e in the present embodiment is formed such that the inner peripheral surface thereof approaches the wrapping portion 64c rather than other portions in the vicinity of the engagement portion 66. Therefore, it is possible to substantially suppress the loosening of the operation wire 30 in the vicinity of the engagement portion 66.

In addition, the guard portion 63e is provided so as to face also the operation wire 30 which is bound to the engagement portion 66 (fixation portion). Therefore, it is also possible to suppress the loosening of the operation wire 30 bound to the engagement portion 66.

In order to more reliably exhibit the above-described effect, it is desirable to bind the operation wire 30 with the engagement portion 66 by inserting the proximal side of the operation wire 30 into a region 67 (refer to FIG. 15C) surrounded by the engagement portion 66, the flange portion 64b, and the guard portion 63e.

In order to have such a configuration, it is preferable that the engagement portion 66 (fixation portion) in the present embodiment be bent to the radial outside of the flange portion 64b. In addition, the guard portion 63e in the present embodiment abuts or approaches the distal portion of the engagement portion 66 and the outer peripheral surface of the flange portion 64b. Moreover, the proximal side of the operation wire 30 is inserted into the region 67 surrounded by the engagement portion 66, the flange portion 64b, and the guard portion 63e, and is bound to the engagement portion 66.

In the above, it has been described that the guard portion 63e does not necessarily abut on the flange portion 64b or the engagement portion 66, and may approach the flange portion and the engagement portion. However, it is preferable that the gap between the inner surface of the guard portion 63e and the outer surface of the flange portion 64b (or the distal portion of the engagement portion 66) be smaller than the diameter dimension of the operation wire 30. This is because the deviation of the loosened operation wire 30 is more reliably prevented.

As shown in FIGS. 15A to 15C, the wire fixation panel 64 (winding portion) includes the flange portion 64b formed on (the side peripheral surface of) the wrapping portion 64c.

The present invention has been described while showing a plurality of embodiments. However, the above-described various components are not essential components. The components may be omitted to the degree to which the effect of the present invention is not impaired, or may be replaced by other components which function or act equally with the components.

In addition, it is not necessary for the various components of the present invention to be independently present. It is possible for a plurality of components to be formed as a member, one component to be formed in a plurality of members, a certain component to be a part of the other component, a part of a certain component to overlap a part of the other component, or the like.

INDUSTRIAL APPLICABILITY

The present invention provides a medical device preventing operation wires which have been loosened through a turning operation from deviating.

REFERENCE SIGNS LIST 100 catheter
10 sheath portion
12 side hole
14 first marker
16 second marker
20 main lumen
22 inner layer
24 reinforcement wire
26 wire-reinforced layer
28 hollow tube
30, 30a, 30b operation wire
32 sub-lumen
34 first outer layer
36 second outer layer
38 outer layer
40 second reinforced layer
42 second reinforcement wire
50 operation portion
60 turning operation portion
61 dial operation portion
61c opening portion
62 limiter member
62a spring engagement portion
62b shaft portion
62c locking convex portion
63 engagement member
63a concavo-convex portion
63b recessed portion
63c penetration portion
63d closing portion
63e guard portion
64 wire fixation panel
64a slit
64b flange portion
64c wrapping portion
64d projection portion
64e, 64g opening portion
64f protrusion portion
65 shaft member
65a rotation shaft
65b, 65c guide rib
65d guide groove
66 engagement portion
67 region
68 claw portion
70 hub connector
80 operation portion main body
81 separation surface
82 upper main body
84 lower main body
84b rear end portion
84h gap
84i intermittent rib
84j inner guide
87 protector
88 lock slider
DE distal portion
PE proximal portion

The invention claimed is:

1. A medical device, comprising:
a sheath having an elongated shape;
a plurality of operation wires extending in the sheath and having a distal end fixed to a distal portion of the sheath; and
a turning operation device positioned on a proximal end side of the sheath and configured to pull a first operation wire of the plurality of operation wires and send out a second operation wire of the plurality of operation wires through a turning operation such that the sheath is bent in a direction corresponding to the first operation wire,
wherein the turning operation device has a winding portion having a side peripheral surface around which the plurality of operation wires are wound, and a plurality of guard portions which are positioned radially outwards with respect to the side peripheral surface of the winding portion such that the plurality of guard portions are facing the side peripheral surface and engaged with the winding portion and that each of the plurality of operation wires extends between a respective one of the plurality of guard portions and the side peripheral surface of the winding portion, the winding portion includes a pair of flange portions formed on the side peripheral surface, and a plurality of opening portions formed in at least one of the pair of flange portions, and the plurality of guard portions project and engage with the plurality of opening portions, respectively.

2. The medical device according to claim 1, wherein the turning operation device has a fitting portion which is fitted to the winding portion in a turning shaft direction of the winding portion, the plurality of guard portions are formed in the fitting portion, and the plurality of guard portions are positioned to face the plurality of operation wires wound around the side peripheral surface through fitting of the fitting portion to the winding portion, and are turnable integrally with the winding portion.

3. The medical device according to claim 1, wherein the plurality of guard portions come into contact with outer peripheral surfaces of the pair of flange portions.

4. The medical device according to claim 1, wherein each of the plurality of guard portions has a separation point at which a respective one of the plurality of operation wires is separated from the side peripheral surface as a reference in an initial state, and each of the plurality of guard portions extends by being biased to a side opposite to a direction in which the respective one of the plurality of operation wires is drawn from the separation point to the sheath.

5. The medical device according to claim 4, wherein the plurality of operation wires are wound around the side peripheral surface over a winding angle which exceeds 360 degrees but does not reach 720 degrees in the initial state, and one of the plurality of guard portions extends by being biased to a side on which the winding using another one of the plurality of operation wires is overlapping.

6. The medical device according to claim 4, wherein the winding portion includes a pair of fixation portions to which proximal sides of the plurality of operation wires are individually fixed, and the plurality of guard portions rotate from one of the pair of fixation portions to the other one of the pair of fixation portions.

7. The medical device according to claim 6, wherein the distance from an inner peripheral surface of one of the plurality of guard portions to the side peripheral surface is made shorter than the distance of another of the plurality of guard portions in the vicinity of the pair of fixation portions.

8. The medical device according to claim 7, wherein one of the pair of flange portions has a pair of notches which is formed inward from an outer peripheral side of the one of the pair of flange portions, the pair of fixation portions are formed on one surface of the one of the pair of flange portions on a side opposite to a surface facing the other one of the pair of flange portions, the plurality of operation wires wound around the side peripheral surface is bound to the pair of fixation portions by being drawn from the pair of notches, respectively, and each of the plurality of guard portions faces a respective one of the plurality of operation wires wound around the side peripheral surface and faces the other one of the plurality of operation wires bound to one of the pair of fixation portions.

9. The medical device according to claim 8, wherein the pair of fixation portions are bent to a radial outside of the pair of flange portions, each of the plurality of guard portions abuts or approaches a distal portion of a respective one of the pair of fixation portions and the outer peripheral surfaces of the pair of flange portions, and the proximal side of each of the plurality of operation wires is inserted into a region surrounded by a respective one of the pair of fixation portions, a respective one of the pair of flange portions, and the respective one of the plurality of guard portions, and is bound to the respective one of the pair of fixation portions.

10. The medical device according to claim 6, wherein a gap between an inner peripheral surface of each of the plurality of guard portions and an outer peripheral surface of each of the pair of flange portions is smaller than a diameter dimension of the plurality of operation wires.

11. The medical device according to claim 1, wherein the pair of flange portions is configured to pinch the side peripheral surface, and each of the plurality of guard portions includes a penetration portion which extends into one of the pair of flange portions to the other one of the pair of flange portions.

12. The medical device according to claim 11, wherein, when the turning operation reaches a predetermined angle, the penetration portion is configured to abut on one of the plurality of operation wires sent out through the turning operation, and the one of the plurality of operation wires is pulled in a rotation direction of the turning operation through the turning operation further exceeding the predetermined angle.

13. The medical device according to claim 12, further comprising:
a pulling amount-limiting device which operates according to a reaction force received from the plurality of operation wires through the turning operation and limits pulling of the one of the plurality of operation wires to be less than or equal to a predetermined amount,
wherein the reaction force which the turning operation device receives from another one of the plurality of operation wires due to the turning operation and the reaction force which the turning operation device receives from the one of the plurality of operation wires in a tensed state by being pulled in the rotation direction due to the turning operation are imparted in a same direction.

14. The medical device according to claim 11, wherein one of the pair of flange portions has a plurality of notches formed inward from an outer peripheral side of the one of the pair of flange portions such that end portions of the plurality of operation wires are drawn from the plurality of notches and are fixed to the winding portion, respectively, each of the plurality of guard portions is configured to close the outer peripheral side of the one of the pair of flange portions such that each of the plurality of guard portions closes the outer peripheral side more outside than a position of the penetration portion and that a gap between each of the plurality of guard portions and a respective one of the plurality of notches is smaller than a diameter dimension of the plurality of operation wires.

15. The medical device according to claim 11, wherein one of the pair of flange portions has a plurality of notches formed inward from an outer peripheral side of the one of the pair of flange portions such that end portions of the plurality of operation wires are drawn from the plurality of notches and are fixed to the winding portion, the pair of flange portions have a separation point at which a respective one of the plurality of operation wires is separated from the side peripheral surface as a reference in an initial state, and the plurality of opening portions includes a plurality of opening portions formed in the other one of the pair of flange portions such that the penetration portion is configured to penetrate a respective one of the plurality of opening portions formed in the other one of the pair of flange portions.

16. The medical device according to claim 15, wherein each of the plurality of guard portions includes a closing portion which closes a respective one of the plurality of notches, and a gap between the respective one of the plurality of notches and the closing portion is smaller than a diameter dimension of the plurality of operation wires.

17. A medical device according to claim 1, wherein the winding portion has a plurality of notches formed inward from an outer peripheral side of one of the pair of flange portions, and an end portion of each of the plurality of operation wires drawn from a respective one of the plurality of notches is fixed to the winding portion, and each of the plurality of guard portions is configured to close the outer peripheral side of the one of the pair of flange portions.

18. The medical device according to claim 17, wherein one of the pair of flange portions has a plurality of notches, each of the plurality of operation wires is fixed to the winding portion by being drawn from a respective one of the plurality of notches, and each of the plurality of guard portions is formed with respect to a respective one of the plurality of notches from which the respective one of the plurality of operation wires is drawn.

19. The medical device according to claim 1, further comprising:
an angle-restricting device configured to restrict the turning operation and comprising a plurality of mechanisms which are engaged with each other when the turning operation reaches a predetermined rotation angle.

* * * * *